US012173056B2

(12) United States Patent
Cui et al.

(10) Patent No.: US 12,173,056 B2
(45) Date of Patent: Dec. 24, 2024

(54) ANTIBODY AGAINST HUMAN CARDIAC TROPONIN I AND USE THEREOF

(71) Applicant: GUAGNDONG FEIPENG BIOLOGICAL CO., LTD., Guangdong (CN)

(72) Inventors: Peng Cui, Guangdong (CN); Zhiqiang He, Guangdong (CN); Yuan Meng, Guangdong (CN); Dongmei Zhong, Guangdong (CN)

(73) Assignee: FAPON BIOTECH INC., Shenzhen (CN)

( * ) Notice: Subject to any disclaimer, the term of this patent is extended or adjusted under 35 U.S.C. 154(b) by 866 days.

(21) Appl. No.: 17/278,345

(22) PCT Filed: Sep. 27, 2019

(86) PCT No.: PCT/CN2019/108689

§ 371 (c)(1),
(2) Date: Mar. 22, 2021

(87) PCT Pub. No.: WO2020/073834

PCT Pub. Date: Apr. 16, 2020

(65) Prior Publication Data

US 2022/0033484 A1 Feb. 3, 2022

(30) Foreign Application Priority Data

Oct. 10, 2018 (CN) ........................ 201811183078.6

(51) Int. Cl.
*C07K 16/18* (2006.01)
*G01N 33/577* (2006.01)
*G01N 33/68* (2006.01)

(52) U.S. Cl.
CPC ........... *C07K 16/18* (2013.01); *G01N 33/577* (2013.01); *G01N 33/6887* (2013.01); *C07K 2317/24* (2013.01); *C07K 2317/31* (2013.01); *C07K 2317/565* (2013.01); *C07K 2317/92* (2013.01); *G01N 2333/4712* (2013.01); *G01N 2470/04* (2021.08)

(58) Field of Classification Search
None
See application file for complete search history.

(56) References Cited

U.S. PATENT DOCUMENTS

2021/0380675 A1* 12/2021 Sachen ................ C07K 16/244

FOREIGN PATENT DOCUMENTS

| | | | |
|---|---|---|---|
| CN | 101942416 | A | 1/2011 |
| CN | 101942416 | B | 3/2012 |
| CN | 103173420 | A | 6/2013 |
| CN | 107603955 | A | 1/2018 |
| JP | 2016141649 | A | 8/2016 |
| WO | 9610076 | A1 | 4/1996 |

OTHER PUBLICATIONS

Gregory Lee et al: "Monoclonal Antibodies Against Human Cardiac Troponin I for Immunoassays II", Monoclonal Antibodies in Immunodiagnosis and Immunotherapy, vol. 34, No. 3, Jun. 1, 2015, pp. 169-173, XP055700550, US ISSN: 2167-9436, DOI: 10.1089/mab.2014.0088.

Conroy P. J. et al: "Cardiac troponin I: a case study in rational antibody design for human diagnostics", Protein Engineering, Design and Selection, vol. 25, No. 6, Apr. 16, 2012, pp. 295-305, XP055859415, GB ISSN: 1741-0126, DOI: 10.1093/protein/gzs018.

Conroy Paul John et al: "Exploiting novel antibodies for the early detection of cardiac disease", Nov. 1, 2011, XP055859422, Retrieved from the Internet: URL:https://core.ac.uk/download/pdf/30933926.pdf [retrieved on Nov. 9, 2021] pp. 5-75 pp. 5-78 pp. 6-9.

N. N.: "Product Information Anti-Human cardiac troponin I (cTnl) mAb (20B3)", Ab-Y-Biotech Online catalogue, Jan. 1, 2011, XP055859430, Retrieved from the Internet: URL:https://abybiotech.com/wp-content/uploads/abybiotech_spec_sheet_20B3.pdf [retrieved on Nov. 9, 2021] the whole document.

Hao, Qingqin et al. "Preparation and Identification of a Pair of High Affinity Monoclonal Antibody Against Human Cardiac Troponin I" Labeled Immunoassays and Clinical Medicine, vol. 21, No. 4, Aug. 25, 2014, pp. 462-465.

Lee,G. and Liu.S "Monoclonal Antibodies Against Human Cardiac Troponin I for Immunoassays II" Monoclonal Antibodies in Immunodiagnosis and Immunotherapy, vol. 34, No. 3, Jun. 30, 2015, pp. 169-173.

* cited by examiner

*Primary Examiner* — Daniel E Kolker
*Assistant Examiner* — James Ryland Melchior
(74) *Attorney, Agent, or Firm* — Samson G. Yu

(57) ABSTRACT

Disclosed is an isolated binding protein including a cardiac troponin I (cTnI) antigen binding domain, and preparation and a use and the like of the binding protein. The antigen binding domain includes at least one complementarity determining region selected from an amino acid sequence defined in this article, or has at least 80% sequence identity with the complementarity determining region of the amino acid sequence and has $KD \leq 9.96 \times 10^{-8}$ mol/L affinity with cTnI. The binding protein may be used in the detection field of the cTnI protein.

19 Claims, No Drawings

Specification includes a Sequence Listing.

ANTIBODY AGAINST HUMAN CARDIAC TROPONIN I AND USE THEREOF

CROSS-REFERENCE TO RELATED APPLICATION

The present application is a National Stage of International Patent Application No: PCT/CN2019/108689 filed on Sep. 27, 2019, which claims the benefit of priority to Chinese Patent Application No. 201811183078.6 filed to the China National Intellectual Property Administration on Oct. 10, 2018 and entitled "Antibody against human cardiac troponin I and use thereof", the disclosure of which is hereby incorporated by reference in its entirety.

SEQUENCE LISTING

The present application contains a Sequence Listing which has been submitted electronically in ASCII format and is hereby incorporated by reference in its entirety. Said ASCII copy is named_Sequence_Listing.txt and is 16.0 kilobytes in size, and contains 16 new sequences from SEQ ID NO:13 to SEQ ID NO:28 described in claims and examples of this file, but not numbered. The original sequences of SEQ ID NO: 1 to SEQ ID NO: 12 are identical to the sequence listing filed in the corresponding international application No. PCT/CN2019/108689 filed on Sep. 27, 2019.

TECHNICAL FIELD

The disclosure relates to the field of biotechnologies and medical technologies, and in particular to an antibody against a human cardiac troponin I and an application thereof.

BACKGROUND

Before the 1980s, myocardial enzyme spectrum activity is always used as one of diagnostic criterion for acute myocardial infarction (AMI) by the World Health Organization (WHO). In the late 1980s, it is discovered by researchers that the sensitivity and specificity of a troponin (Tn) are higher than that of biomarkers such as a creatine phosphokinase (CK), a creatine phosphokinase isoenzyme (CK-MB), a lactic dehydrogenase and an aspartate aminotransferase. A cardiac troponin I (cTnI) exists only in a myocardium and is a label of myocardial cells, and abnormal changes thereof may affect diastolic and systolic functions of a heart, and may be used for diagnosing myocardial necrosis, judging myocardial damage and the like. The cardiac troponin I becomes one of the most sensitive and specific labels of cardiomyocyte damage, and is recognized as a major biochemical mark for rapidly diagnosing AMI and acute coronary syndromes (ACS), as well as assisting in risk stratification of the ACS and reflecting its prognosis.

The content of the cTnI in blood of a normal person is less than 0.3 μg/L generally. While the integrity of a myocardial cell membrane is damaged due to ischemia or hypoxia, the free cTnI may quickly penetrate through the cell membrane and enter a bloodstream. Therefore, the rapid, sensitive and accurate determination of the cTnI in human blood and a change trend thereof in the early stage of a disease has the important clinical significance to the diagnosis of acute myocardial infarction, the risk stratification of the acute coronary syndrome, and the monitoring of myocardial injury caused by various factors and the like. Clinical methods used to detect cTnI levels include an enzyme-linked immunosorbent assay (ELISA), chemiluminescence, colloidal gold and the like. The different methods have own advantages and disadvantages, but they all require specific monoclonal antibodies against the cTnI.

Existing cTnI antibodies may not be well applied to the detection of the cTnI protein due to low activity and poor affinity. Therefore, there is a strong demand in the art for an antibody which effectively and specifically binds and detects the cTnI and detects it.

SUMMARY

The disclosure relates to a novel isolated binding protein including a cardiac troponin I (cTnI) antigen binding domain, and researches in aspects of preparation and a use and the like of the binding protein.

The antigen binding domain includes at least one complementarity determining region selected from the following amino acid sequences, or has at least 80% sequence identity with the complementarity determining region of the following amino acid sequences and has KD<$9.96\times10^{-8}$ mol/L affinity with the cTnI;

a complementarity determining region CDR-VH1 is G-Y-X1-F-T-X2-Y-V-X3-H (SEQ ID NO:13), herein, the X1 is S or T, X2 is I or L, and the X3 is V, L or I;

a complementarity determining region CDR-VH2 is Y-I-X1-P-Y-X2-D-G-T-X3-Y-N-E-K (SEQ ID NO:14), herein, the X1 is Q, N or Y, the X2 is I or L, and the X3 is R or K;

a complementarity determining region CDR-VH3 is R-X1-G-Y-G-X2-Y-G-L-A (SEQ ID NO:15), herein, the X1 is S or T, and the X2 is Q, N or G;

a complementarity determining region CDR-VL1 is S-X1-G-A-X2-T-T-S-X3-Y-A-N (SEQ ID NO:16), herein, the X1 is S or T, the X2 is A or V, and the X3 is Q or N;

a complementarity determining region CDR-VL2 is G-S-X1-N-R-X2-P (SEQ ID NO: 17), herein the X1 is N or Q, and the X2 is A or V;

a complementarity determining region CDR-VL3 is A-X1-V-Y-S-N-X2-W (SEQ ID NO: 18), herein, the X1 is I or L, and the X2 is Q, H or N.

An important advantage is that the binding protein has the strong activity, and has very high affinity and very high sensitivity with the human cTnI.

In one or more implementation modes, in the complementarity determining region CDR-VH1, the X1 is T;

in the complementarity determining region CDR-VH2, the X3 is K;

in the complementarity determining region CDR-VH3, the X1 is S;

in the complementarity determining region CDR-VL1, the X1 is T;

in the complementarity determining region CDR-VL2, the X2 is A; and in the complementarity determining region CDR-VL3, the X1 is L.

In one or more implementation modes, in the complementarity determining region CDR-VH1, the X2 is I, and the X3 is V.

In one or more implementation modes, in the complementarity determining region CDR-VH1, the X2 is I, and the X3 is L.

In one or more implementation modes, in the complementarity determining region CDR-VH1, the X2 is I, and the X3 is I.

In one or more implementation modes, in the complementarity determining region CDR-VH1, the X2 is L, and the X3 is V.

In one or more implementation modes, in the complementarity determining region CDR-VH1, the X2 is L, and the X3 is L.

In one or more implementation modes, in the complementarity determining region CDR-VH1, the X2 is L, and the X3 is I.

In one or more implementation modes, in the complementarity determining region CDR-VH2, the X1 is Q, and the X2 is I.

In one or more implementation modes, in the complementarity determining region CDR-VH2, the X1 is Q, and the X2 is L.

In one or more implementation modes, in the complementarity determining region CDR-VH2, the X1 is N, and the X2 is I.

In one or more implementation modes, in the complementarity determining region CDR-VH2, the X1 is N, and the X2 is L.

In one or more implementation modes, in the complementarity determining region CDR-VH2, the X1 is Y, and the X2 is I.

In one or more implementation modes, in the complementarity determining region CDR-VH2, the X1 is Y, and the X2 is L.

In one or more implementation modes, in the complementarity determining region CDR-VH3, the X2 is Q.

In one or more implementation modes, in the complementarity determining region CDR-VH3, the X2 is N.

In one or more implementation modes, in the complementarity determining region CDR-VH3, the X2 is G.

In one or more implementation modes, in the complementarity determining region CDR-VL1, the X2 is A, and the X3 is Q.

In one or more implementation modes, in the complementarity determining region CDR-VL1, the X2 is A, and the X3 is N.

In one or more implementation modes, in the complementarity determining region CDR-VL1, the X2 is V, and the X3 is Q.

In one or more implementation modes, in the complementarity determining region CDR-VL1, the X2 is V, and the X3 is N.

In one or more implementation modes, in the complementarity determining region CDR-VL2, the X1 is N.

In one or more implementation modes, in the complementarity determining region CDR-VL2, the X1 is Q.

In one or more implementation modes, in the complementarity determining region CDR-VL3, the X2 is Q.

In one or more implementation modes, in the complementarity determining region CDR-VL3, the X2 is H.

In one or more implementation modes, in the complementarity determining region CDR-VL3, the X2 is N.

In one or more implementation modes, a mutation site of each complementarity determining region is selected from any one of the following mutation combinations:

| Site | CDR-VH1 X2/X3 | CDR-VH2 X1/X2 | CDR-VH3 X2 | CDR-VL1 X2/X3 | CDR-VL2 X1 | CDR-VL3 X2 |
|---|---|---|---|---|---|---|
| Mutation combination 1 | L/V | Q/L | G | A/Q | N | H |
| Mutation combination 2 | I/L | Q/I | N | A/N | Q | Q |
| Mutation combination 3 | I/I | Q/I | G | V/Q | N | N |
| Mutation combination 4 | L/V | Q/I | Q | V/N | Q | Q |
| Mutation combination 5 | L/L | Q/I | N | A/Q | N | N |
| Mutation combination 6 | L/I | Q/I | G | A/N | Q | H |
| Mutation combination 7 | I/V | Q/L | Q | V/Q | N | N |
| Mutation combination 8 | I/L | Q/L | N | V/N | Q | H |
| Mutation combination 9 | I/I | Q/L | G | A/Q | N | Q |
| Mutation combination 10 | L/V | Q/L | Q | A/N | Q | H |
| Mutation combination 11 | L/L | Q/L | N | V/Q | N | Q |
| Mutation combination 12 | L/I | N/I | G | V/N | Q | N |
| Mutation combination 13 | I/V | N/I | Q | A/Q | N | Q |
| Mutation combination 14 | I/L | N/I | N | A/N | Q | N |
| Mutation combination 15 | I/I | N/I | G | V/Q | N | H |
| Mutation combination 16 | L/V | N/I | Q | V/N | Q | N |
| Mutation combination 17 | L/L | N/L | N | A/Q | N | H |
| Mutation combination 18 | L/I | N/L | G | A/N | Q | Q |
| Mutation combination 19 | I/V | N/L | Q | V/Q | N | H |
| Mutation combination 20 | IL | N/L | N | V/N | Q | Q |
| Mutation combination 21 | I/I | Y/I | G | A/Q | N | N |
| Mutation combination 22 | L/V | Y/I | Q | A/N | Q | Q |
| Mutation combination 23 | L/L | Y/I | N | V/Q | N | N |
| Mutation combination 24 | L/I | Y/I | G | V/N | Q | H |
| Mutation combination 25 | I/V | Y/L | Q | A/Q | N | N |
| Mutation combination 26 | I/L | Y/L | N | A/N | Q | H |
| Mutation combination 27 | I/I | Y/L | G | V/Q | N | Q |
| Mutation combination 28 | L/V | Y/L | Q | V/N | Q | H |
| Mutation combination 29 | L/L | Y/L | N | A/Q | N | Q |
| Mutation combination 30 | L/I | Q/I | G | A/Q | Q | N |
| Mutation combination 31 | I/V | Q/L | Q | A/Q | N | Q |
| Mutation combination 32 | I/L | N/I | N | A/Q | Q | N |
| Mutation combination 33 | I/I | N/L | G | A/N | N | H |
| Mutation combination 34 | L/V | Y/I | G | A/Q | Q | N |
| Mutation combination 35 | L/L | Q/I | N | A/N | N | H |
| Mutation combination 36 | L/I | Q/L | G | A/N | Q | Q |
| Mutation combination 37 | I/V | N/I | Q | V/Q | N | H |
| Mutation combination 38 | I/L | N/L | N | V/Q | Q | Q |

-continued

| Site | CDR-VH1 X2/X3 | CDR-VH2 X1/X2 | CDR-VH3 X2 | CDR-VL1 X2/X3 | CDR-VL2 X1 | CDR-VL3 X2 |
|---|---|---|---|---|---|---|
| Mutation combination 39 | I/I | Y/I | G | V/Q | N | N |
| Mutation combination 40 | L/V | Q/L | Q | V/N | Q | Q |
| Mutation combination 41 | I/L | Q/L | N | V/N | N | N |
| Mutation combination 42 | L/I | N/I | N | V/N | Q | Q |
| Mutation combination 43 | L/V | N/L | Q | V/N | N | H |
| Mutation combination 44 | I/L | Y/I | N | A/Q | Q | Q |
| Mutation combination 45 | I/I | Q/I | G | A/N | N | N |
| Mutation combination 46 | L/IV | Q/L | Q | V/Q | Q | Q |
| Mutation combination 47 | I/L | N/I | N | V/N | N | N |
| Mutation combination 48 | L/I | N/L | G | A/Q | Q | H |
| Mutation combination 49 | I/V | Y/I | Q | A/N | N | Q |
| Mutation combination 50 | L/L | N/L | N | V/Q | Q | N |
| Mutation combination 51 | I/I | Y/I | G | V/N | Q | H |
| Mutation combination 52 | I/V | Q/I | Q | A/Q | N | H |
| Mutation combination 53 | I/V | N/L | N | A/Q | N | N |
| Mutation combination 54 | I/V | Y/I | G | V/N | Q | Q |
| Mutation combination 55 | I/V | N/L | Q | A/N | N | Q |
| Mutation combination 56 | I/V | Y/I | G | V/Q | Q | N |

In one or more implementation modes, the binding protein includes at least 3 CDRs; or the binding protein includes at least 6 CDRs.

In one or more implementation modes, the binding protein is a complete antibody including a variable region and a constant region.

In one or more implementation modes, the binding protein is one of a nano-antibody, F(ab')2, Fab', Fab, Fv, scFv, a bispecific antibody and an antibody minimum recognition unit.

In one or more implementation modes, the binding protein includes light-chain framework regions FR-L1, FR-L2, FR-L3 and FR-L4 of which sequences are successively shown in SEQ ID NO: 1-4, and/or heavy-chain framework regions FR-H1, FR-H2, FR-H3 and FR-H4 of which sequences are successively shown in SEQ ID NO: 5-8.

In one or more implementation modes, the binding protein further includes an antibody constant region sequence.

In one or more implementation modes, the constant region sequence is selected from a sequence of any one constant region of IgG1, IgG2, IgG3, IgG4, IgA, IgM, IgE, and IgD.

In one or more implementation modes, a species source of the constant region is cattle, horse, dairy cow, pig, sheep, goat, rat, mouse, dog, cat, rabbit, camel, donkey, deer, mink, chicken, duck, goose, turkey, gamecock or human.

In one or more implementation modes, the constant region is derived from the mouse;

a light-chain constant region sequence is as shown in SEQ ID NO: 9; and a heavy-chain constant region sequence is as shown in SEQ ID NO: 10.

The disclosure further provides an isolated nucleic acid, and the above binding protein is encoded by the nucleic acid.

The disclosure further provides a vector, and the vector includes the above nucleic acid.

The disclosure further provides a host cell, and the host cell includes the above nucleic acid or vector.

The disclosure further provides a method for producing the above binding protein, including the following steps.

The above host cell is cultured in a culture medium, and the generated binding protein is recovered from the culture medium or from the cultured host cells.

The disclosure further provides a use of the above binding protein in preparing a diagnostic agent or a kit for diagnosing acute myocardial infarction, acute coronary syndrome, pulmonary infarction, unstable angina pectoris, and myocardial injury.

According to one aspect of the disclosure, the disclosure further relates to a method for detecting a troponin I antigen in a test sample, including:

a) in a condition sufficient for an antibody/antigen binding reaction, enabling the troponin I antigen in the test sample to contact with the binding protein to form an immune complex; and b) detecting the presence of the immune complex, the presence of the immune complex indicates the presence of the troponin I antigen in the test sample.

In one or more implementation modes, the troponin I antigen is a cardiac troponin I antigen.

In one or more implementation modes, in the step a), the immune complex further includes a second antibody, and the second antibody is bound with the binding protein.

In one or more implementation modes, in the step a), the immune complex further includes a second antibody, and the second antibody is bound with the troponin I antigen.

As in some further improvements, the disclosure further provides a kit, and the kit includes one or more of the above binding protein, the above nucleic acid or the above vector.

The disclosure further relates to a use of the binding protein described herein in diagnosing a disease related to a cardiac troponin I.

The disclosure further relates to a method for diagnosing a disease related to a cardiac troponin I, including:

A) in a condition sufficient for a binding reaction, enabling a sample from a subject to contact with the binding protein of the present disclosure to perform the binding reaction; and B) detecting an immune complex generated by the binding reaction, herein, the presence of the immune complex indicates the presence of the disease related to the cardiac troponin I.

In one or more implementation modes, the method is based on a fluorescence immunoassay, a chemiluminescence technology, a colloidal gold immunotechnology, a radioimmunoassay and/or an enzyme-linked immunoassay.

In one or more implementation modes, the sample is selected from at least one of whole blood, peripheral blood, serum, plasma or a myocardial tissue.

In one or more implementation modes, the subject is a mammal, for example a primate, and for example a human.

In one or more implementation modes, the disease related to the cardiac troponin I is a cardiovascular disease.

In one or more implementation modes, the disease related to the cardiac troponin I is selected from a group consisting of acute myocardial infarction, acute coronary syndrome, pulmonary infarction, unstable angina pectoris, myocardial injury or a combination thereof.

DETAILED DESCRIPTION OF THE EMBODIMENTS

The disclosure may be more easily understood through the following description of some embodiments of the disclosure and the detailed content of the embodiments included therein.

Before the disclosure is further described, it should be understood that the disclosure may not be limited to specific implementation schemes, because these implementation schemes are diverse necessarily. It should also be understood that terms used in the description are only intended to illustrate the specific implementation schemes, rather than intended as limitation, because a scope of the disclosure may be defined in appended claims.

Unless otherwise defined herein, the scientific and technical terms used in connection with the disclosure shall have the meanings commonly understood by those of ordinary skill in the art. The meaning and scope of the terms should be clear, however, in the case of any potential ambiguity, definitions provided herein take precedence over any dictionaries or foreign definitions. In the present application, the use of "or" means "and/or" unless otherwise specified. In addition, the use of a term "including" and other forms is non-restrictive.

Generally, a nomenclature and a technology thereof used in connection with cell and tissue culture, molecular biology, immunology, microbiology, genetics and protein and nucleic acid chemistry and hybridization described herein are those well known and commonly used in the art. Unless otherwise specified, methods and technologies of the disclosure are generally performed according to conventional methods well known in the art and as described in various general and more specific references, and the references are cited and discussed throughout the description. An enzymatic reaction and a purification technology are performed according to instructions of a manufacturer, as commonly achieved in the art or as described herein. The nomenclature used in connection with analytical chemistry, synthetic organic chemistry, and medical and pharmaceutical chemistry described herein, as well as laboratory procedures and technologies thereof are those well known and commonly used in the art.

In order to more easily understand the disclosure, the terms selected are defined below.

A term "amino acid" refers to a naturally existing or non-naturally existing carboxyl-a-amino acid. The term "amino acid" used in the present application may include a naturally existing amino acid and a non-naturally existing amino acid. The naturally existing amino acid includes an alanine (three-letter code: A1a, and single-letter code: A), an arginine (Arg, R), an asparagine (Asn, N), an aspartic acid (Asp, D), a cysteine (Cys, c), a glutamine (Gln, Q), a glutamic acid (Glu, E), a glycine (Gly, G), a histidine (His, H), an isoleucine (IIe, I), an leucine (Leu, L), an lysine (Lys, K), a methionine (Met, M), a phenylalanine (Phe, F), a proline (Pro, P), a serine (Ser, S), a threonine (Thr, T), a tryptophan (Trp, W), a tyrosine (Tyr, Y), and a valine (Val, V). The non-naturally existing amino acid includes but is not limited to a α-aminoadipate, an aminobutyric acid, a citrulline, a homocitrulline, a homoleucine, a homoarginine, a hydroxyproline, a norleucine, a pyridyl alanine, a sarcosine and the like.

A term "isolated binding protein" is a protein that, because a derived origin or a source thereof is not bound with a naturally-bound component, it is accompanied by the naturally-bound component in a natural state thereof; other proteins from the same species are basically not contained; it is expressed by cells from the different species; or it does not exist in the nature. Therefore, a protein synthesized chemically or synthesized in a cell system different from a natural origin thereof may be "isolated" from the naturally-bound component thereof. It may also be isolated, for example, a protein purification technology well known in the art is used, so that the naturally-bound component is basically not contained in the protein.

A term "isolated binding protein including an antigen binding domain" broadly refers to all proteins/protein fragments containing CDR regions. A term "antibody" includes a polyclonal a monoclonal antibody, antibody, and antigen-compound-binding fragments of these antibodies, including Fab, F(ab')2, Fd, Fv, scFv, a bispecific antibody, and a minimum recognition unit, and single-chain derivatives of these antibodies and fragments. A type of the antibody may select IgG1, IgG2, IgG3, IgG4, IgA, IgM, IgE, and IgD. In addition, the term "antibody" includes a naturally existing antibody and a non-naturally existing antibody, including, for example, chimeric, bifunctional and humanized antibodies, and related synthetic isoforms. The term "antibody" may be used interchangeably with "immunoglobulin".

The "variable region" or "variable domain" of the antibody refers to an amino terminal domain of the heavy-chain or the light-chain of the antibody. The variable domain of the heavy-chain may be referred to as "VH". The variable domain of the light-chain may be referred to as "VL". These domains are usually the most variable parts of the antibody and contain antigen binding sites. The variable region of the light-chain or the heavy-chain is composed of three hypervariable regions called "complementarity determining region" or "CDR" and a framework region for separating them. The framework region of the antibody, namely an architecture region which constitutes a combination of the light-chain and the heavy-chain of a key component, has a function of positioning and aligning the CDR, and the CDR is mainly responsible for binding to the antigen.

As used herein, "framework region", "architecture region" or "FR" means a region, excluding those regions defined as the CDR, of the antibody variable domains. Each antibody variable domain framework region may be further subdivided into adjacent regions (FR1, FR2, FR3, and FR4) isolated by the CDRs.

Usually, the variable regions VL/VH of the heavy-chain and the light-chain may be acquired by arranging and connecting the following numbered CDRs and FRs in the following combination: FR1-CDR1-FR2-CDR2-FR3-CDR3-FR4.

As used herein, a term "purified" or "isolated" associated with a polypeptide or a nucleic acid means that the polypeptide or the nucleic acid is not in a natural medium thereof or in a natural form. Therefore, the term "isolated" includes the polypeptide or the nucleic acid taken from an original environment thereof, for example, from the natural environment if it is naturally existing. For example, an isolated polypeptide usually does not contain at least some proteins or other cellular components which are usually bound with it or usually mixed with it or in solution. The isolated polypeptide includes the naturally generated polypeptide contained in a cell lysate, the polypeptide in purified or partially purified form, a recombinant polypeptide, the polypeptide expressed or secreted by cells, and the polypeptide in a heterologous host cell or a culture. Associated with the nucleic acid, the term isolated or purified indicates, for example, that the nucleic acid is not in a natural genomic background thereof (for example, in a vector, as an expression cassette, linked to a promoter, or artificially introduced into the heterologous host cell).

As used herein, a term "bispecific antibody" or "bifunctional antibody" refers to an artificial hybrid binding protein with two different pairs of heavy/light-chain and two different binding sites. The bispecific binding protein may be generated by a variety of methods, including fusion of hybridomas or linking of Fab' fragments.

As used herein, a term "sequence identity" refers to the similarity between at least two different sequences. This percentage identity may be determined by a standard algorithm, such as a Basic Local Alignment Search Tool (BLAST); an algorithm such as Needleman; or an algorithm such as Meyers. In one or more implementation modes, a set of parameters may be a Blosum 62 scoring matrix and a gap penalty 12, a gap extension penalty 4, and a frameshift gap penalty 5. In one or more implementation modes, the percentage identity between two amino acids or nucleotide sequences may also be determined by using an algorithm of Meyers and Miller ((1989) CABIOS 4:11-17), the algorithm is already incorporated into an ALIGN program (version 2.0), a PAM120 weight residue table, a gap length penalty 12, and a gap penalty 4 are used. The percentage identity is usually calculated by comparing sequences with a similar length.

As used herein, a term "affinity" refers to the binding strength of the antigen binding domain of the binding protein or the antibody and an antigen or an epitope. The affinity may be measured by a KD value. The KD value is smaller, it is represented that the affinity is greater.

The disclosure provides an isolated binding protein including an antigen binding domain, the antigen binding domain includes at least one complementarity determining region selected from the following amino acid sequences, or has at least 80% sequence identity with the complementarity determining region of the following amino acid sequences and has $K_D \geq 9.96\times10^{-8}$ mol/L affinity with a cTnI;

a complementarity determining region CDR-VH1 is G-Y-X1-F-T-X2-Y-V-X3-H (SEQ ID NO:13), herein, the X1 is S or T, X2 is I or L, and the X3 is V, L or I;

a complementarity determining region CDR-VH2 is Y-I-X1-P-Y-X2-D-G-T-X3-Y-N-E-K (SEQ ID NO:14), herein, the X1 is Q, N or Y, the X2 is I or L, and the X3 is R or K;

a complementarity determining region CDR-VH3 is R-X1-G-Y-G-X2-Y-G-L-A (SEQ ID NO:15), herein, the X1 is S or T, and the X2 is Q, N or G;

a complementarity determining region CDR-VL1 is S-X1-G-A-X2-T-T-S-X3-Y-A-N(SEQ ID NO:16), herein, the X1 is S or T, the X2 is A or V, and the X3 is Q or N;

a complementarity determining region CDR-VL2 is G-S-X1-N-R-X2-P (SEQ ID NO: 17), herein the X1 is N or Q, and the X2 is A or V;

a complementarity determining region CDR-VL3 is A-X1-V-Y-S-N-X2-W (SEQ ID NO: 18), herein, the X1 is I or L, and the X2 is Q, H or N.

It is well known in the art that the binding specificity and affinity of the antibody are mainly determined by the CDR sequences. According to mature and well-known existing various technologies, the amino acid sequence of a non-CDR region may be easily changed to obtain a variant with the similar biological activity. Therefore, the disclosure also includes a "functional derivative" of the binding protein. The "functional derivative" refers to a variant substituted by an amino acid. One functional derivative retains detectable binding protein activity, preferably the activity of an antibody capable of binding the cTnI. The "functional derivative" may include a "variant" and a "fragment", because it has exactly the same CDR sequence as the binding protein described in the disclosure, and therefore it has the similar biological activity.

In one or more implementation modes, the antigen binding domain has at least 50%, or at least 55%, or at least 60%, or at least 65%, or at least 70%, or at least 75%, or at least 80%, or at least 85%, or at least 90%, or at least 91%, or at least 92%, or at least 93%, or at least 94%, or at least 95%, or at least 96%, or at least 97%, or at least 98%, or at least 99% sequence identity with the complementarity determining regions of the following amino acid sequences, and has $KD \leq 9.96\times10^{-8}$ mol/L affinity with the cardiac troponin I, the KD value may also be selected from $2.26\times10^{-8}$ mol/L, $6.76\times10^{-8}$ mol/L, $3.54\times10^{-8}$ mol/L, $9.41\times10^{-9}$ mol/L, $7.95\times10^{-9}$ mol/L, $5.41\times10^{-9}$ mol/L, $4.20\times10^{-9}$ mol/L, $1.08\times10^{-9}$ mol/L, $8.66\times10^{-10}$ mol/L, $6.97\times10^{-10}$ mol/L, $3.99\times10^{-10}$ mol/L $1.06\times10^{-10}$ mol/L, or $1.06\times10^{-10}$ mol/L$\leq KD \leq 9.96\times10^{-8}$ mol/L, or $1.06\times10^{-10}$ mol/L$\leq KD \leq 9.41\times10^{-9}$ mol/L; or KD is less than or equal to $2.26\times10^{-8}$ mol/L, $6.76\times10^{-8}$ mol/L, $3.54\times10^{-8}$ mol/L, $9.41\times10^{-9}$ mol/L, $7.95\times10^{-9}$ mol/L, $5.41\times10^{-9}$ mol/L, $4.20\times10^{-9}$ mol/L, $1.08\times10^{-9}$ mol/L, $8.66\times10^{-10}$ mol/L, $6.97\times10^{-10}$ mol/L, $3.99\times10^{-10}$ mol/L or $1.06\times10^{-10}$ mol/L.

Herein, the affinity is measured according to a method in the description of the disclosure.

In one or more implementation modes, in the complementarity determining region CDR-VH1, the X1 is T;

in the complementarity determining region CDR-VH2, the X3 is K;

in the complementarity determining region CDR-VH3, the X3 is S;

in the complementarity determining region CDR-VL1, the X3 is T;

in the complementarity determining region CDR-VL2, the X2 is A; and in the complementarity determining region CDR-VL3, the X1 is L.

In one or more implementation modes, in the complementarity determining region CDR-VH1, the X2 is I, and the X3 is V.

In one or more implementation modes, in the complementarity determining region CDR-VH1, the X2 is I, and the X3 is L.

In one or more implementation modes, in the complementarity determining region CDR-VH1, the X2 is I, and the X3 is I.

In one or more implementation modes, in the complementarity determining region CDR-VH1, the X2 is L, and the X3 is V.

In one or more implementation modes, in the complementarity determining region CDR-VH1, the X2 is L, and the X3 is L.

In one or more implementation modes, in the complementarity determining region CDR-VH1, the X2 is L, and the X3 is I.

In one or more implementation modes, in the complementarity determining region CDR-VH2, the X1 is Q, and the X2 is I.

In one or more implementation modes, in the complementarity determining region CDR-VH2, the X1 is Q, and the X2 is L.

In one or more implementation modes, in the complementarity determining region CDR-VH2, the X1 is N, and the X2 is I.

In one or more implementation modes, in the complementarity determining region CDR-VH2, the X1 is N, and the X2 is L.

In one or more implementation modes, in the complementarity determining region CDR-VH2, the X1 is Y, and the X2 is I.

In one or more implementation modes, in the complementarity determining region CDR-VH2, the X1 is Y, and the X2 is L.

In one or more implementation modes, in the complementarity determining region CDR-VH3, the X2 is Q.

In one or more implementation modes, in the complementarity determining region CDR-VH3, the X2 is N.

In one or more implementation modes, in the complementarity determining region CDR-VH3, the X2 is G.

In one or more implementation modes, in the complementarity determining region CDR-VL1, the X2 is A, and the X3 is Q.

In one or more implementation modes, in the complementarity determining region CDR-VL1, the X2 is A, and the X3 is N.

In one or more implementation modes, in the complementarity determining region CDR-VL1, the X2 is V, and the X3 is Q.

In one or more implementation modes, in the complementarity determining region CDR-VL1, the X2 is V, and the X3 is N.

In one or more implementation modes, in the complementarity determining region CDR-VL2, the X1 is N.

In one or more implementation modes, in the complementarity determining region CDR-VL2, the X1 is Q.

In one or more implementation modes, in the complementarity determining region CDR-VL3, the X2 is Q.

In one or more implementation modes, in the complementarity determining region CDR-VL3, the X2 is H.

In one or more implementation modes, in the complementarity determining region CDR-VL3, the X2 is N.

In one or more implementation modes, a mutation site of each complementarity determining region is selected from any one of the following mutation combinations:

| Site | CDR-VH1 X2/X3 | CDR-VH2 X1/X2 | CDR-VH3 X2 | CDR-VL1 X2/X3 | CDR-VL2 X1 | CDR-VL3 X2 |
|---|---|---|---|---|---|---|
| Mutation combination 1 | L/V | Q/L | G | A/Q | N | H |
| Mutation combination 2 | I/L | Q/I | N | A/N | Q | Q |
| Mutation combination 3 | I/I | Q/I | G | V/Q | N | N |
| Mutation combination 4 | L/V | Q/I | Q | V/N | Q | Q |
| Mutation combination 5 | L/L | Q/I | N | A/Q | N | N |
| Mutation combination 6 | L/I | Q/I | G | A/N | Q | H |
| Mutation combination 7 | I/V | Q/L | Q | V/Q | N | N |
| Mutation combination 8 | I/L | Q/L | N | V/N | Q | H |
| Mutation combination 9 | I/I | Q/L | G | A/Q | N | Q |
| Mutation combination 10 | L/V | Q/L | Q | A/N | Q | H |
| Mutation combination 11 | L/L | Q/L | N | V/Q | N | Q |
| Mutation combination 12 | L/I | N/I | G | V/N | Q | N |
| Mutation combination 13 | I/V | N/I | Q | A/Q | N | Q |
| Mutation combination 14 | I/L | N/I | N | A/N | Q | N |
| Mutation combination 15 | I/I | N/I | G | V/Q | N | H |
| Mutation combination 16 | L/V | N/I | Q | V/N | Q | N |
| Mutation combination 17 | L/L | N/L | N | A/Q | N | H |
| Mutation combination 18 | L/I | N/L | G | A/N | Q | Q |
| Mutation combination 19 | I/V | N/L | Q | V/Q | N | H |
| Mutation combination 20 | IL | N/L | N | V/N | Q | Q |
| Mutation combination 21 | I/I | Y/I | G | A/Q | N | N |
| Mutation combination 22 | L/V | Y/I | Q | A/N | Q | Q |
| Mutation combination 23 | L/L | Y/I | N | V/Q | N | N |
| Mutation combination 24 | L/I | Y/I | G | V/N | Q | H |
| Mutation combination 25 | I/V | Y/L | Q | A/Q | N | N |
| Mutation combination 26 | I/L | Y/L | N | A/N | Q | H |
| Mutation combination 27 | I/I | Y/L | G | V/Q | N | Q |
| Mutation combination 28 | L/V | Y/L | Q | V/N | Q | H |
| Mutation combination 29 | L/L | Y/L | N | A/Q | N | Q |
| Mutation combination 30 | L/I | Q/I | G | A/Q | Q | N |
| Mutation combination 31 | I/V | Q/L | Q | A/Q | N | Q |
| Mutation combination 32 | I/L | N/I | N | A/Q | Q | N |
| Mutation combination 33 | I/I | N/L | G | A/N | N | H |
| Mutation combination 34 | L/V | Y/I | G | A/Q | Q | N |
| Mutation combination 35 | L/L | Q/I | N | A/N | N | H |
| Mutation combination 36 | L/I | Q/L | G | A/N | Q | Q |
| Mutation combination 37 | I/V | N/I | Q | V/Q | N | H |
| Mutation combination 38 | I/L | N/L | N | V/Q | Q | Q |
| Mutation combination 39 | II | Y/I | G | V/Q | N | N |
| Mutation combination 40 | L/V | Q/L | Q | V/N | Q | Q |
| Mutation combination 41 | I/L | Q/L | N | V/N | N | N |
| Mutation combination 42 | L/I | N/I | N | V/N | Q | Q |
| Mutation combination 43 | L/V | N/L | Q | V/N | N | H |
| Mutation combination 44 | I/L | Y/I | N | A/Q | Q | Q |
| Mutation combination 45 | I/I | Q/I | G | A/N | N | N |
| Mutation combination 46 | L/V | Q/L | Q | V/Q | Q | Q |
| Mutation combination 47 | I/L | N/I | N | V/N | N | N |
| Mutation combination 48 | L/I | N/L | G | A/Q | Q | H |

-continued

| Site | CDR-VH1 X2/X3 | CDR-VH2 X1/X2 | CDR-VH3 X2 | CDR-VL1 X2/X3 | CDR-VL2 X1 | CDR-VL3 X2 |
|---|---|---|---|---|---|---|
| Mutation combination 49 | I/V | Y/I | Q | A/N | N | Q |
| Mutation combination 50 | L/L | N/L | N | V/Q | Q | N |
| Mutation combination 51 | I/I | Y/I | G | V/N | Q | H |
| Mutation combination 52 | I/V | Q/I | Q | A/Q | N | H |
| Mutation combination 53 | I/V | N/L | N | A/Q | N | N |
| Mutation combination 54 | I/V | Y/I | G | V/N | Q | Q |
| Mutation combination 55 | I/V | N/L | Q | A/N | N | Q |
| Mutation combination 56 | I/V | Y/I | G | V/Q | Q | N |

In one or more implementation modes, the X1 appearing in the six CDR regions of the binding protein described in the disclosure each independently represents the amino acid defined in the disclosure; the X2 appearing in the six CDR regions of the binding protein described in the disclosure each independently represents the amino acid defined in the disclosure; and the X3 appearing in the six CDR regions of the binding protein described in the disclosure each independently represents the amino acid defined in the disclosure.

In one or more implementation modes, the binding protein includes at least 3 CDRs; or the binding protein includes at least 6 CDRs.

In one or more implementation modes, the binding protein is a complete antibody including a variable region and a constant region.

In one or more implementation modes, the binding protein is one of a nano-antibody, F(ab')2, Fab', Fab, Fv, scFv, a bispecific antibody and an antibody minimum recognition unit.

In one or more implementation modes, the binding protein includes light-chain framework regions FR-L1, FR-L2, FR-L3 and FR-L4 of which sequences are successively shown in SEQ ID NO: 1-4, and/or heavy-chain framework regions FR-H1, FR-H2, FR-H3 and FR-H4 of which sequences are successively shown in SEQ ID NO: 5-8.

In one or more implementation modes, the binding protein further includes an antibody constant region sequence.

In one or more implementation modes, the constant region sequence is selected from a sequence of any one constant region of IgG1, IgG2, IgG3, IgG4, IgA, IgM, IgE, and IgD.

In one or more implementation modes, a species source of the constant region is cattle, horse, dairy cow, pig, sheep, goat, rat, mouse, dog, cat, rabbit, camel, donkey, deer, mink, chicken, duck, goose, turkey, gamecock or human.

In one or more implementation modes, the constant region is derived from the mouse;

a light-chain constant region sequence is as shown in SEQ ID NO: 9; and a heavy-chain constant region sequence is as shown in SEQ ID NO: 10.

The disclosure further provides an isolated nucleic acid, and the above binding protein is encoded by the nucleic acid.

In this article, the nucleic acid includes a conservatively substituted variant thereof (for example, substitution of a degenerate codon) and a complementary sequence. The terms "nucleic acid" and "polynucleotide" are synonymous and include a gene, a cDNA molecule, an mRNA molecule and their fragments such as an oligonucleotide.

The disclosure further provides a vector, and the vector includes the above nucleic acid.

The nucleic acid sequence therein is operably linked with at least one regulatory sequence. The "operably linked" means that a coding sequence is linked with the regulatory sequence in a mode that the expression of the coding sequence is allowed. The regulatory sequence is selected to direct the expression of a target protein in a suitable host cell, and includes a promoter, an enhancer and other expression control elements.

In this article, the vector may refer to a molecule or an agent which contains the nucleic acid of the disclosure or a fragment thereof, may carry genetic information and may deliver the genetic information to cells. Typical vectors include a plasmid, a virus, a bacteriophage, a cosmid and a minichromosome. The vector may be a cloning vector (namely, a vector used to transfer the genetic information to a cell, the cell may be propagated and the cell with or without the genetic information may be selected) or an expression vector (namely, a vector which contains a necessary genetic element so that the genetic information of the vector is allowed to be expressed in the cell). Therefore, the cloning vector may contain a selection label and an origin of replication which is matched with a cell type specified by the cloning vector, and the expression vector may contain a regulatory element necessary for affecting the expression in a specified target cell.

The nucleic acid of the disclosure or the fragment thereof may be inserted into a suitable vector to form the cloning vector or the expression vector carrying the nucleic acid fragment of the disclosure. This new vector is also a part of the disclosure. The vector may include the plasmid, the bacteriophage, the cosmid, the minichromosome or the virus, and also include a naked DNA which is only transiently expressed in a specific cell. The cloning vector and the expression vector of the disclosure may be replicated spontaneously, and therefore a high copy number may be provided for a purpose of high-level expression or high-level replication for subsequent cloning. The expression vector may include a promoter for driving the expression of the nucleic acid fragment of the disclosure, an optional nucleic acid sequence for encoding a signal peptide which enables a peptide expression product to be secreted or integrated to a membrane, the nucleic acid fragment of the disclosure, and an optional nucleic acid sequence for encoding a terminator. While the expression vector is operated in a production strain or a cell line, the vector may be integrated to a genome of a host cell while it is introduced into the host cell, or it may not be integrated to the genome of the host cell. The vector usually carries a replication site, and a label sequence which may provide phenotypic selection in a transformed cell.

The expression vector of the disclosure is used to transform the host cell. Such a transformed cell is also a part of the disclosure, and may be used to proliferate the nucleic acid fragment and the vector of the disclosure, or used to recombinantly prepare cultured cells or cell lines of the polypeptide of the disclosure. The transformed cell of the disclosure includes a microorganism such as bacteria (such as *Escherichia coli, bacillus*). The host cell also includes a cell from a multicellular organism such as fungi, an insect cell, a plant cell or a mammalian cell, preferably a cell from a mammal, such as a CHO cell. The transformed cell is capable of replicating the nucleic acid fragment of the disclosure. While the peptide combination of the disclosure is recombinantly prepared, the expression product may be exported to a culture medium or carried on the surface of the transformed cell.

The disclosure further provides a method for producing the above binding protein, including the following steps.

The above host cells are cultured in a culture medium, and the generated binding protein is recovered from the culture medium or from the cultured host cells.

The method may be that, for example, a nucleic acid vector encoding at least a part of the binding protein is used to transfect a host cell, and the host cell is cultured in a suitable condition so that the binding protein is expressed by it. The host cell may also be transfected with one or more expression vectors, and the expression vector may alone or connectively contain a DNA encoding at least a part of the binding protein. The binding protein may be isolated from the culture medium or the cell lysate by using a conventional technology for purifying the protein and the peptide, and the technology includes ammonium sulfate precipitation, chromatography (such as ion exchange, gel filtration, affinity chromatography) and/or electrophoresis.

The construction of the suitable vector containing the target coding and regulatory sequence may be performed by using a standard linkage and restriction technology well-known in the art. The isolated plasmid, the DNA sequence or the synthetic oligonucleotide is cut, tailed and re-linked in a needed form. Any methods may be used to introduce mutations into the coding sequence to generate the variant of the disclosure, and these mutations may include deletion or insertion or substitution and the like.

The disclosure also provides an antibody which may react with an epitope of the cTnI, including monoclonal and polyclonal antibodies. The antibody may contain a complete binding protein, or a fragment or derivative thereof. The preferred antibody contains all or part of the binding protein.

The disclosure further provides a use of the above binding protein in preparing a diagnostic agent or a kit for diagnosing acute myocardial infarction, acute coronary syndrome, pulmonary infarction, unstable angina pectoris, and myocardial injury.

According to one aspect of the disclosure, the disclosure further relates to a method for detecting a troponin I antigen in a test sample, including:

a) in a condition sufficient for an antibody/antigen binding reaction, enabling the troponin I antigen in the test sample to contact with the binding protein to form an immune complex; and b) detecting the presence of the immune complex, the presence of the immune complex indicates the presence of the troponin I antigen in the test sample.

In this implementation mode, the binding protein may be labeled by an indicator which shows signal intensity, so that the complex may be easily detected.

In one or more implementation modes, the troponin I antigen is a cardiac troponin I antigen.

In one or more implementation modes, in the step a), the immune complex further includes a second antibody, and the second antibody is bound with the binding protein;

in this implementation mode, the binding protein forms a paired antibody with the second antibody in the form of the first antibody, and it is used for binding to the different epitopes of the cTnI; and the second antibody may be labeled by the indicator which shows the signal intensity, so that the complex may be easily detected.

In one or more implementation modes, in the step a), the immune complex further includes a second antibody, and the second antibody is bound with the troponin I antigen; and in this implementation mode, the binding protein is served as an antigen of the second antibody, the second antibody may be labeled by the indicator which shows the signal intensity, so that the complex may be easily detected.

In one or more implementation modes, the indicator which shows the signal intensity includes any one of a fluorescent substance, a quantum dot, a digoxigenin-labeled probe, a biotin, a radioisotope, a radiocontrast agent, a paramagnetic ion fluorescent microsphere, an electron dense substance, a chemiluminescence label, an ultrasound contrast agent, a photosensitizer, a colloidal gold, or an enzyme.

In one or more implementation modes, the fluorescent substance includes any one of Alexa 350, Alexa 405, Alexa 430, Alexa 488, Alexa 555, Alexa 647, AMCA, aminoacridine, BODIPY 630/650, BODIPY 650/665, BODIPY-FL, BODIPY-R6G, BODIPY-TMR, BODIPY-TRX, 5-carboxyl-4',5'-dichloro-2',7'-dimethoxyfluorescein, 5-carboxyl-2',4',5',7'-tetrachlorofluorescein, 5-carboxyfluorescein, 5-carboxyrhodamine, 6-carboxyrhodamine, 6-carboxytetramethylrhodamine, Cascade Blue, Cy2, Cy3, Cy5, Cy7, 6-FAM, Dansyl chloride, fluorescein, HEX, 6-JOE, NBD (7-nitrobenzo-2-oxa-1,3-diazole), Oregon Green 488, Oregon Green 500, Oregon Green514, Pacific Blue, phthalic acid, terephthalic acid, isophthalic acid, cresol solid violet, cresol blue violet, brilliant cresol blue, p-aminobenzoic acid, erythrosine, phthalocyanine, azomethine, cyanine, xanthine, succinyl fluorescein, rare earth metal cryptate, triple pyridyl diamine europium, europium cryptate or chelate, diamine, dicyanin, La Jolla blue dye, allophycocyanin, allocyanin B, phycocyanin C, phycocyanin R, thiamine, phycoerythrin, phycoerythrin R, REG, Rhodamine Green, rhodamine isothiocyanate, Rhodamine Red, ROX, TAMRA, TET, TRIT (Tetramethyl Rhodamine Isothiol), tetramethylrhodamine or Texas Red.

In one or more implementation modes, the radioisotope includes any one of $^{110}$In, $^{111}$In, $^{177}$Lu, $^{18}$F, $^{52}$Fe, $^{62}$Cu, $^{64}$Cu, $^{67}$Cu, $^{67}$Ga, $^{68}$Ga, $^{86}$Y, $^{90}$Y, $^{89}$Zr, $^{94}$m Tc, $^{94}$Tc, $^{94}$m Tc, $^{120}$I, $^{123}$I, $^{124}$I, $^{125}$I, $^{131}$I, $^{154-158}$Gd, $^{32}$p, $^{11}$C, $^{13}$N, $^{15}$O, $^{186}$Re, $^{188}$Re, $^{51}$Mn, $^{52}$mMn, $^{55}$Co, $^{72}$As, $^{75}$Br, $^{76}$Br, $^{82}$mRb or $^{83}$Sr.

In one or more implementation modes, the enzyme includes any one of a horseradish peroxidase, an alkaline phosphatase or a glucose oxidase.

In one or more implementation modes, the fluorescent microsphere is: a polystyrene fluorescent microsphere, and the rare earth fluorescent ion europium is wrapped inside.

Further, the disclosure further provides a kit, and the kit includes one or more of the above binding protein, the above isolated nucleic acid or the above vector.

Preferably, the kit further includes a label for labeling the binding protein.

As in some embodiments, the disclosure provides, for example, a kit for determining the presence of the troponin I in a subject with a cardiomyocyte infection, the kit includes at least one of the binding proteins provided in the disclosure, a related buffer, a reagent required for reacting a liquid sample with the binding protein, and a reagent for determining whether there is a positive or negative binding reaction between the troponin I and the binding protein. In order to determine the presence of the troponin I, the kit may, for example, use a binding protein with a label as an antibody, herein the label may be any suitable labels, such as a colloidal gold label.

The disclosure further relates to an application of the binding protein described herein in diagnosing a disease related to a cardiac troponin I.

A term "disease related to a cardiac troponin I" as used herein refers to a disease which uses the cardiac troponin I, including a protein or an encoding nucleic acid thereof, as a marker. In particular, in one or more implementation modes of the disclosure, the disease related to the cardiac troponin I may refer to a disease characterized by an increased level of the cardiac troponin I in blood. In one or more implementation modes of the disclosure, the disease related to the cardiac troponin I may refer to a disease characterized by a decreased level of the cardiac troponin I in a cardiac tissue or a cardiomyocyte.

The disclosure further relates to a method for diagnosing a disease related to a cardiac troponin I, including:

A) in a condition sufficient for a binding reaction, enabling a sample from a subject to contact with the binding protein of the disclosure to perform the binding reaction; and B) detecting an immune complex generated by the binding reaction, herein, the presence of the immune complex indicates the presence of the disease related to the cardiac troponin I.

In one or more implementation modes, the method is based on a fluorescence immunoassay, a chemiluminescence technology, a colloidal gold immunotechnology, a radioimmunoassay and/or an enzyme-linked immunoassay.

In one or more implementation modes, the sample is selected from at least one of whole blood, peripheral blood, serum, plasma or a myocardial tissue.

In one or more implementation modes, the subject is a mammal, for example a primate, and for example a human.

In one or more implementation modes, the disease related to the cardiac troponin I is a cardiovascular disease.

In one or more implementation modes, the disease related to the cardiac troponin I is selected from a group consisting of acute myocardial infarction, acute coronary syndrome, pulmonary infarction, unstable angina pectoris, myocardial injury or a combination thereof.

Some embodiments are provided below to illustrate the disclosure, but not to limit a scope of the disclosure.

Embodiment 1

In the embodiment, a restriction endonuclease and a Prime Star DNA polymerase are purchased from the Takara Company. A MagExtractor-RNA extraction kit is purchased from the TOYOBO Company. An SMARTER™ RACE cDNA Amplification Kit is purchased from the Takara Company. A pMD-18T vector is purchased from the Takara Company. A plasmid extraction kit is purchased from the Tiangen Company. Primer synthesis and gene sequencing are completed by the Invitrogen Company. A hybridoma cell strain that secretes an Anti-cTnI-21C5 monoclonal antibody is an existing hybridoma cell strain of our company, and is resuscitated for future use.

1. Primer

```
5'RACE primer for amplifying heavy-chain and
light-chain:
SMARTER II A oligonucleotide:
                                    (SEQ ID NO: 19)
5'-AAGCAGTGGTATCAACGCAGAGTACXXXXX-3';

5'-RACE CDS primer (5-CDS):
```

-continued

```
                                    (SEQ ID NO: 20)
5'-(T)25VN-3' (N = A, C, G, or T; V = A, G, or C);

universal primer A mixture (UPM):
                                    (SEQ ID NO: 21)
5'-CTAATACGACTCACTATAGGGCAAGCAGTGGTATCAACGCAGAGT-
3';

nested universal primer A (NUP):
                                    (SEQ ID NO: 22)
5'-AAGCAGTGGTATCAACGCAGAGT-3';

MIgG-CKR:
                                    (SEQ ID NO: 23)
5'-CGCCTAACACTCATTCCTGTTGAAGC-3';
and

MIgG-CHR:
                                    (SEQ ID NO: 24)
5'-CCGCTCATTTACCCGGAGACCG-3'.
```

2. Gene Cloning and Sequencing of Antibody Variable Region

A RNA is extracted from the hybridoma cell strain secreting the Anti-cTnI 21C5 monoclonal antibody, and the synthesis of a first chain cDNA is performed by using the SMARTER™ RACE cDNA Amplification Kit and the SMARTER II A oligonucleotide and 5'-CDS primer in the kit, an obtained first chain cDNA product is used as a PCR amplification template. A light-chain gene is amplified with the universal primer A mixture (UPM), the nested universal primer A (NUP) and the MIgG-CKR primer, and a heavy-chain gene is amplified with the universal primer A mixture (UPM), the nested universal primer A (NUP) and the MIgG-CHR primer. Herein a primer pair of the light-chain amplifies a target band of about 0.7 KB, and a primer pair of the heavy-chain amplifies a target band of about 1.4 KB. It is purified and recovered by using agarose gel electrophoresis, and the product is subjected to an A-adding reaction with the rTaq DNA polymerase and inserted into the pMD-18T vector, and transformed into a DH5a competent cell, after a bacterial colony is grown, the heavy-chain and light-chain genes are respectively cloned, and 4 clones each are sent to the Invitrogen Company for sequencing.

3. Sequence Analysis of Variable Region Genes of Anti-cTnI 21 C5 Antibody

The gene sequence obtained by the above sequencing is put in an IMGT antibody database for analysis, and VNTI11.5 software is used to analyze and determine that the genes amplified by the heavy-chain and light-chain primer pairs are all correct, herein in the gene fragment amplified by the light-chain, the VL gene sequence is 357 bp, and belongs to a VkII gene family, and there is a 57 bp leader peptide sequence in front of it; and in the gene fragment amplified by the heavy-chain primer pair, the VH gene sequence is 366 bp, and belongs to a VH1 gene family, and there is a 57 bp leader peptide sequence in front of it.

4. Construction of Recombinant Antibody Expression Plasmid

The pcDNA™ 3.4 TOPO® vector is a constructed recombinant antibody eukaryotic expression vector. Multiple cloning restriction sites such as HindIII, BamHI, and EcoRI were introduced into this expression vector, and is named as the pcDNA 3.4A expression vector, and referred to as the 3.4A expression vector later; As a result of the antibody gene sequencing in the above pMD-18T, specific primers of the heavy-chain and light-chain genes of the Anti-cTnI 21C5 antibody are designed, and two ends are respectively provided with the HindIII and EcoRI restriction sites and protective bases, and the primers are as follows:

```
cTnI-21C5-HF:
                                              (SEQ ID NO: 25)
5.-CCCAAGCTTGCCGCCACCATGAGTGTGCTCACTCAGGTCCTGGGGT-

3';

cTnI-21C5-HR:
                                              (SEQ ID NO: 26)
5'-GGGGAATTCTCATTTACCCGGAGACCGGGAGATGGTCTTC-3';

cTnI-21C5-LF:
                                              (SEQ ID NO: 27)
5'-CCCAAGCTTGCCGCCACCATGAAGTCACAGACCAGGTCTTCGTA-3';
and

cTnI-21C5-LR:
                                              (SEQ ID NO: 28)
5'-CCCGAATTCTCAACACTCATTCCTGTTGAAGCTCTTGACGATG-3'.
```

The 0.73 KB light-chain gene fragment and 1.45 KB heavy-chain gene fragment are amplified by a PCR amplification method. The heavy-chain and light-chain gene fragments are double-digested with HindIII/EcoRI respectively, and the 3.4A vector is double-digested with the HindIII/EcoRI, after the fragment and vector are purified and recovered, the heavy-chain gene and the light-chain gene are linked in the 3.4A expression vector respectively, and the recombinant expression plasmids of the heavy-chain and light-chain are respectively obtained.

5. Screening of Stable Cell Lines 5.1. The plasmids are diluted to 400 ng/ml with ultrapure water, the CHO cells are adjusted to $1.43\times10^7$ cells/ml in a centrifuge tube, 100 μl of the plasmids are mixed with 700 μl of the cells, and transferred to an electroporation cup for electroporation, sampling and counting are performed on the 3-th, 5-th and 7-th days, and a sample is received and detected on the 7-the day.

The corresponding antigens are diluted to a specified concentration with coating solution, 100 μL per well, and overnight at 4 DEG C; on the next day, it is washed twice with washing solution, and patted dry; blocking solution (20% BSA+80% PBS) is added, 120 μL per well, 37 DEG C, and 1 h, and patted dry; diluted cell supernatant is added, 100 μL/well, 37 DEG C, and 30 min (partial supernatant, 1h); it is washed for 5 times with the washing solution, and patted dry; goat anti-mouse IgG-HRP is added, 100 μL per well, 37 DEG C, and 30 min; it is washed for 5 times with the washing solution, and patted dry; color developing solution A (50 μL/well) is added, color developing solution B (50 μL/well) is added, 10 min; stop solution is added, 50 μL/well; and an OD value is read at 450 nm (refer to 630 nm) on a microplate reader. The antibody content in the cell supernatant is calculated by using the standard concentration and the OD value as a standard curve.

5.2. Recombinant Antibody Expression Plasmid Linearization

The following reagents are prepared: 50 μl of a Buffer, 100 μg/tube of a DNA, 10 μl of a Puvl enzyme, sterile water supplemented to 500 μl, a water bath at 37 DEG C, and enzyme-digested overnight; an equal volume of phenol/chloroform/isoamyl alcohol (lower layer) 25:24:1 is used firstly, and then chloroform (aqueous phase) is used for sequential extraction; 0.1 times of 3M sodium acetate in volume (aqueous phase) and 2 times of ethanol in volume are precipitated on ice, a precipitation is rinsed with 70% ethanol, an organic solvent is removed, an appropriate amount of the sterile water is used for re-melting until the ethanol is completely evaporated, and finally the concentration is measured.

The recombinant antibody expression plasmids are stably transfected, and stable cell strains are screened under a pressure:

The plasmids are diluted to 400 ng/ml with the ultrapure water, the CHO cells are adjusted to $1.43\times10^7$ cells/ml in a centrifuge tube, 100 μl of the plasmids are mixed with 700 μl of cells, and transferred to an electroporation cup for electroporation, counting is performed on the next day; and it is cultured for about 25 days under the pressure in 25 μmol/L of an MSX 96-well.

Cloning wells in which cells are grown are observed and marked under a microscope, and a confluence degree is recorded; culture supernatant is taken, and a sample is sent for detection; cell strains with high antibody concentration and relative concentration are selected and transferred to a 24-well, and transferred to a 6-well after about 3 days; seed preservation and batch culture are performed after 3 days, a cell density is adjusted to $0.5\times10^6$ cells/ml, the batch culture is performed for 2.2 ml, and the cell density is adjusted to $0.3\times10^6$ cells/ml, the seed preservation is performed for 2 ml; the supernatant is batch-cultured for 7 days in the 6-well and a sample is sent for detection, cell strains with smaller antibody concentration and cell diameter are selected and transferred to a TPP for seed preservation and passage.

6. Recombinant Antibody Generation 6.1. Cell Amplification Culture

After being resuscitated, the cells are firstly cultured in 125 ml of a shake flask, an inoculation volume is 30 ml, and the culture medium is a 100% Dynamis medium, the shake flask is placed in a shaker with 120 r/min of a rotation speed, 37 DEG C of a temperature and 8% of a carbon dioxide. It is cultured for 72 hours, and it is inoculated and amplification-cultured at 500,000 cells/ml of an inoculation density, an amplification culture volume is calculated according to generation requirements, and the culture medium is the 100% Dynamis medium. After that, the amplification culture is performed every 72 h. While a cell amount meets the generation requirements, the inoculation density is strictly controlled to about 500,000 cells/ml for the generation.

6.2. Shake Flask Generation and Purification

Shake flask parameters: 120 r/min of a rotating speed, 37 DEG C of a temperature, 8% of a carbon dioxide. Fed-batch cultivation: feeding is started every day while it is cultured for 72 h in the shake flask, HyClone™ Cell Boost™ Feed 7a is fed with 3% of a fed-batch initial culture volume every day, and a fed-batch amount of Feed 7b in everyday is thousandth of the initial culture volume, it is fed until the 12-th day (feeding on the 12-th day). 3 g/L of glucose is supplemented on the sixth day. A sample is collected on the 13-th day. A protein A affinity chromatography column is used for affinity purification. After the purification, 500 mg of a recombinant antibody is obtained, and 4 μg of the purified antibody is subjected to reducibility SDS-PAGE. Two bands are shown after the reducibility SDS-PAGE, one is a light-chain of about 23 KD (a sequence is as shown in SEQ ID NO: 11), and the other is a heavy-chain of about 50 KD (a sequence is as shown in SEQ ID NO: 12).

Embodiment 2

Although an antibody of Sample 1 (having a light-chain and a heavy-chain of which sequences as shown in SEQ ID NO: 11 and 12) obtained in Embodiment 1 has the ability of binding to a cTnI protein, the affinity and antibody activity are not ideal, so the light-chain CDR and the heavy-chain CDR of the antibody are mutated by the applicant.

After being analyzed, a complementarity determining region (WT) of the heavy-chain:

```
CDR-VH is
                                        (SEQ ID NO: 13)
G-Y-S(X1)-F-T-L(X2)-Y-V-V(X3)-H;

CDR-VH2 is
                                        (SEQ ID NO: 14)
Y-I-Q(X1)-P-Y-L(X2)-D-G-T-R(X3)-Y-N-E-K;

CDR-VH3 is
                                        (SEQ ID NO: 15)
R-T(X1)-G-Y-G-G(X2)-Y-G-L-A;
```

a complementarity determining region of the light-chain:

```
CDR-VL1 is
                                        (SEQ ID NO: 16)
S-S(X1)-G-A-A(X2)-T-T-S-Q(X3)-Y-A-N;

CDR-VL2 is
                                        (SEQ ID NO: 17)
G-S-N(X1)-N-R-V(X2)-P;

CDR-VL3 is
                                        (SEQ ID NO: 18)
A-I(X1)-V-Y-S-N-H(X2)-W;
```

herein, the X1, X2, and X3 are all mutation sites.

TABLE 1 mutation sites related to antibody activity

| Site | CDR-VH1 X1 | CDR-VH2 X3 | CDR-VH3 X1 | CDR-VL1 X1 | CDR-VL2 X2 | CDR-VL3 X1 |
|---|---|---|---|---|---|---|
| WT | S | R | T | S | V | I |
| Mutation 1 | T | K | S | T | A | L |
| Mutation 2 | S | K | S | T | V | I |
| Mutation 3 | T | H | S | S | I | A |
| Mutation 4 | I | F | I | L | N | V |
| Mutation 5 | R | T | R | F | E | Y |

After mutation, the antibody activity is detected. 1 μg/ml of goat anti-mouse IgG is diluted with coating solution to coat a microwell plate, 100 μL per well, and overnight at 4 DEG C; on the next day, it is washed twice with washing solution, and patted dry; blocking solution (20% BSA+80% PBS) is added, 120 μL per well, 37 DEG C, and 1 h, and patted dry; a diluted cTnI monoclonal antibody is added, 100 μL/well, 37 DEG C, and 60 min; liquid in the plate is shaken off, patted dry, and 20% of mouse negative blood is added for blocking, 120 μl per well, 37 DEG C, 1 h; liquid in the plate is shaken off, patted dry, a diluted cTnI antigen (0.15 μg/ml) is added, 100 μL per well, 37 DEG C, and 40 min; it is washed for 5 times with the washing solution, and patted dry; another strain of the cTnI monoclonal antibody (1:5K) labeled with HRP is added, 100 μL per well, 37 DEG C, and 30 min; color developing solution A (50 μL/well) is added, color developing solution B (50 μL/well) is added, 10 min; stop solution is added, 50 μL/well; and a OD value is read at 450 nm (refer to 630 nm) on a microplate reader.

Some of results are as follows:

TABLE 2 antibody activity analysis data

| Concentration (ng/ml) | WT | Mutation 1 | Mutation 2 | Mutation 3 | Mutation 4 | Mutation 5 |
|---|---|---|---|---|---|---|
| 37.037 | 2.162 | 2.326 | 2.095 | 1.578 | 0.821 | 0.478 |
| 12.346 | 1.968 | 2.243 | 1.942 | 0.824 | 0.119 | 0.110 |
| 4.115 | 1.187 | 1.888 | 1.512 | 0.347 | — | — |
| 1.372 | 0.612 | 0.940 | 0.421 | 0.150 | — | — |
| 0.457 | 0.365 | 0.524 | 0.211 | — | — | — |
| 0.000 | 0.130 | 0.114 | 0.117 | — | — | — |

"—" represents no activity.

It may be observed from the above table that Mutation 1 has the best activity, so the Mutation 1 is served as a framework sequence to screen mutation sites with the better titer (it is guaranteed that the antibody activity obtained by screening is similar to that of the Mutation 1, the antibody activity±10%), and some of results are as follows.

TABLE 3

Mutation sites related to antibody affinity

| Site | CDR-VH1 X2/X3 | CDR-VH2 X1/X2 | CDR-VH3 X2 | CDR-VL1 X2/X3 | CDR-VL2 X1 | CDR-VL3 X2 |
|---|---|---|---|---|---|---|
| Mutation 1 | L/V | Q/L | G | A/Q | N | H |
| Mutation 1-1 | I/L | Q/I | N | A/N | Q | Q |
| Mutation 1-2 | I/I | Q/I | G | V/Q | N | N |
| Mutation 1-3 | L/V | Q/I | Q | V/N | Q | Q |
| Mutation 1-4 | L/L | Q/I | N | A/Q | N | N |
| Mutation 1-5 | L/I | Q/I | G | A/N | Q | H |
| Mutation 1-6 | I/V | Q/L | Q | V/Q | N | N |
| Mutation 1-7 | I/L | Q/L | N | V/N | Q | H |
| Mutation 1-8 | I/I | Q/L | G | A/Q | N | Q |
| Mutation 1-9 | L/V | Q/L | Q | A/N | Q | H |
| Mutation 1-10 | L/L | Q/L | N | V/Q | N | Q |
| Mutation 1-11 | L/I | N/I | G | V/N | Q | N |
| Mutation 1-12 | I/V | N/I | N | A/N | N | Q |
| Mutation 1-13 | I/L | N/I | N | A/N | Q | N |
| Mutation 1-14 | I/I | N/I | G | V/Q | N | H |
| Mutation 1-15 | L/V | N/I | Q | V/N | Q | N |
| Mutation 1-16 | L/L | N/L | N | A/Q | N | H |
| Mutation 1-17 | L/I | N/L | G | A/N | Q | Q |
| Mutation 1-18 | I/V | N/L | Q | V/Q | N | H |
| Mutation 1-19 | I/L | N/L | N | V/N | Q | Q |
| Mutation 1-20 | I/I | Y/I | G | A/Q | N | N |
| Mutation 1-21 | L/V | Y/I | Q | A/N | Q | Q |
| Mutation 1-22 | L/L | Y/I | N | V/Q | N | N |
| Mutation 1-23 | L/I | Y/I | G | V/N | Q | H |
| Mutation 1-24 | I/V | Y/L | Q | A/Q | N | N |
| Mutation 1-25 | I/L | Y/L | N | A/N | Q | H |
| Mutation 1-26 | I/I | Y/L | G | V/Q | N | Q |
| Mutation 1-27 | L/V | Y/L | Q | V/N | Q | H |
| Mutation 1-28 | L/L | Y/L | N | A/Q | N | Q |
| Mutation 1-29 | L/I | Q/I | G | A/Q | Q | N |
| Mutation 1-30 | I/V | Q/L | Q | A/Q | N | Q |
| Mutation 1-31 | I/L | N/I | N | A/Q | Q | N |
| Mutation 1-32 | I/I | N/L | G | A/N | N | H |
| Mutation 1-33 | L/V | Y/I | G | A/Q | Q | N |
| Mutation 1-34 | L/L | Q/I | N | A/N | N | H |
| Mutation 1-35 | L/I | Q/L | G | A/N | Q | Q |
| Mutation 1-36 | I/V | N/I | Q | VQ | N | H |
| Mutation 1-37 | I/L | N/L | N | V/Q | Q | Q |
| Mutation 1-38 | I/I | Y/I | G | V/Q | N | N |
| Mutation 1-39 | L/V | Q/L | Q | V/N | Q | Q |
| Mutation 1-40 | I/L | Q/L | N | V/N | N | N |
| Mutation 1-41 | L/I | N/I | N | V/N | Q | Q |
| Mutation 1-42 | L/V | N/L | Q | V/N | N | H |
| Mutation 1-43 | I/L | Y/I | N | A/Q | Q | Q |
| Mutation 1-44 | I/I | Q/I | G | A/N | N | N |
| Mutation 1-45 | L/V | Q/L | Q | V/Q | Q | Q |
| Mutation 1-46 | I/L | N/I | N | V/N | N | N |
| Mutation 1-47 | L/I | N/L | G | A/Q | Q | H |

TABLE 3-continued

| Mutation sites related to antibody affinity | | | | | | |
|---|---|---|---|---|---|---|
| Site | CDR-VH1 X2/X3 | CDR-VH2 X1/X2 | CDR-VH3 X2 | CDR-VL1 X2/X3 | CDR-VL2 X1 | CDR-VL3 X2 |
| Mutation 1-48 | I/V | Y/I | Q | A/N | N | Q |
| Mutation 1-49 | L/L | N/L | N | V/Q | Q | N |
| Mutation 1-50 | I/I | Y/I | G | A/Q | Q | H |
| Mutation 1-51 | I/V | Q/I | Q | A/Q | N | H |
| Mutation 1-52 | I/V | N/L | N | A/Q | N | N |
| Mutation 1-53 | I/V | Y/I | G | V/N | Q | Q |
| Mutation 1-54 | I/V | N/L | Q | A/N | N | Q |
| Mutation 1-55 | I/V | Y/I | G | V/Q | Q | N |

Affinity Analysis

An AMC sensor is used, a purified antibody is diluted to 10 μg/ml with PBST, and a cTnI quality control product recombinant protein (a recombinant antigen generated by a company itself) is diluted with the PBST: 769.2 nmol/ml, 384.6 nmol/ml, 192.3 nmol/ml, 96.2 nmol/ml, 48.1 nmol/ml, 24 nmol/ml, 12 nmol/ml, and 0 nmol/ml.

Operating process: it is equilibrated in Buffer 1 (PBST) for 60 s, the antibody is immobilized in an antibody solution for 300 s, incubated in Buffer 2 (PBST) for 180 s, bound in antigen solution for 420 s, dissociated in the Buffer 2 for 1200 s, 10 mM of GLY solution with pH 1.69 and Buffer 3 are used for sensor regeneration, and data is output. KD represents an equilibrium dissociation constant, namely the affinity; Kon represents a binding rate; and Kdis represents a dissociation rate.

TABLE 4

| Affinity analysis data | | | |
|---|---|---|---|
| Group | KD (M) | Kon (1/Ms) | Kdis (1/S) |
| Mutation 1 | 4.20E−09 | 5.10E+04 | 2.14E−04 |
| Mutation 1-1 | 8.27E−09 | 8.61E+04 | 7.12E−04 |
| Mutation 1-2 | 7.64E−09 | 7.99E+04 | 6.10E−04 |
| Mutation 1-3 | 3.99E−10 | 2.39E+04 | 9.54E−06 |
| Mutation 1-4 | 5.03E−09 | 4.62E+04 | 2.32E−04 |
| Mutation 1-5 | 1.20E−09 | 3.68E+04 | 4.40E−05 |
| Mutation 1-6 | 6.97E−10 | 7.66E+04 | 5.34E−05 |
| Mutation 1-7 | 2.77E−09 | 6.36E+04 | 1.76E−04 |
| Mutation 1-8 | 9.31E−09 | 2.62E+04 | 2.44E−04 |
| Mutation 1-9 | 5.43E−09 | 4.42E+04 | 2.40E−04 |
| Mutation 1-10 | 7.31E−10 | 5.63E+04 | 4.12E−05 |
| Mutation 1-11 | 4.23E−09 | 3.35E+04 | 1.42E−04 |
| Mutation 1-12 | 7.69E−09 | 7.92E+04 | 6.09E−04 |
| Mutation 1-13 | 1.39E−10 | 2.73E+04 | 3.79E−06 |
| Mutation 1-14 | 8.66E−10 | 2.55E+04 | 2.21E−05 |
| Mutation 1-15 | 7.59E−10 | 6.19E+04 | 4.70E−05 |
| Mutation 1-16 | 6.48E−09 | 3.43E+04 | 2.22E−04 |
| Mutation 1-17 | 7.37E−09 | 3.21E+04 | 2.37E−04 |
| Mutation 1-18 | 9.31E−09 | 6.30E+04 | 5.86E−04 |
| Mutation 1-19 | 4.81E−09 | 5.70E+04 | 2.74E−04 |
| Mutation 1-20 | 7.74E−09 | 7.00E+04 | 5.42E−04 |
| Mutation 1-21 | 1.47E−09 | 3.88E+04 | 5.71E−05 |
| Mutation 1-22 | 1.06E−10 | 2.70E+04 | 2.86E−06 |
| Mutation 1-23 | 8.49E−09 | 4.16E+04 | 3.53E−04 |
| Mutation 1-24 | 6.30E−10 | 5.74E+04 | 3.62E−05 |
| Mutation 1-25 | 6.60E−09 | 8.03E+04 | 5.30E−04 |
| Mutation 1-26 | 4.65E−10 | 3.98E+04 | 1.85E−05 |
| Mutation 1-27 | 3.53E−10 | 2.07E+04 | 7.31E−06 |
| Mutation 1-28 | 1.76E−09 | 8.96E+04 | 1.58E−04 |
| Mutation 1-29 | 3.80E−09 | 5.45E+04 | 2.07E−04 |
| Mutation 1-30 | 3.71E−09 | 5.95E+04 | 2.20E−04 |
| Mutation 1-31 | 9.41E−09 | 3.61E+04 | 3.40E−04 |
| Mutation 1-32 | 7.65E−10 | 6.93E+04 | 5.30E−05 |
| Mutation 1-33 | 7.95E−09 | 4.17E+04 | 3.31E−04 |
| Mutation 1-34 | 3.41E−09 | 5.80E+04 | 1.98E−04 |
| Mutation 1-35 | 8.32E−10 | 5.18E+04 | 4.31E−05 |

TABLE 4-continued

| Affinity analysis data | | | |
|---|---|---|---|
| Group | KD (M) | Kon (1/Ms) | Kdis (1/S) |
| Mutation 1-36 | 3.29E−09 | 3.60E+04 | 1.18E−04 |
| Mutation 1-37 | 5.21E−09 | 3.99E+04 | 2.08E−04 |
| Mutation 1-38 | 2.54E−10 | 6.77E+04 | 1.72E−05 |
| Mutation 1-39 | 1.08E−09 | 4.36E+04 | 4.72E−05 |
| Mutation 1-40 | 1 85E−09 | 2.19E+04 | 4.05E−05 |
| Mutation 1-41 | 7.89E−09 | 8.20E+04 | 6.47E−04 |
| Mutation 1-42 | 8.21E−10 | 8.28E+04 | 6.80E−05 |
| Mutation 1-43 | 4.64E−10 | 7.29E+04 | 3.38E−05 |
| Mutation 1-44 | 6.56E−09 | 3.13E+04 | 2.05E−04 |
| Mutation 1-45 | 7.41E−09 | 3.86E+04 | 2.86E−04 |
| Mutation 1-46 | 5.41E−09 | 4.01E+04 | 2.17E−04 |
| Mutation 1-47 | 3.05E−09 | 6.41E+04 | 1.96E−04 |
| Mutation 1-48 | 5.53E−10 | 7.82E+04 | 4.32E−05 |
| Mutation 1-49 | 1.51E−09 | 8.84E+04 | 1.34E−04 |
| Mutation 1-50 | 4.61E−09 | 5.05E+04 | 2.33E−04 |
| Mutation 1-51 | 7.30E−09 | 3.05E+04 | 2.23E−04 |
| Mutation 1-52 | 6.01E−09 | 8.18E+04 | 4.92E−04 |
| Mutation 1-53 | 8.38E−09 | 6.48E+04 | 5.43E−04 |
| Mutation 1-54 | 7.78E−09 | 4.13E+04 | 3.21E−04 |
| Mutation 1-55 | 4.31E−09 | 5.54E+04 | 2.39E−04 |

It may be seen from Table 4 that the mutation sites listed in Table 3 have a little effect on the affinity of the antibody.

In order to verify the above result, the above experiment is repeated by using WT as a framework sequence, the affinity of the mutation sites is verified, and some of results are as follows;

TABLE 5

| mutation performed by using WT as framework | | | | | | |
|---|---|---|---|---|---|---|
| Site | CDR-VH1 X2/X3 | CDR-VH2 X1/X2 | CDR-VH3 X2 | CDR-VL1 X2/X3 | CDR-VL2 X1 | CDR-VL3 X2 |
| WT | L/V | Q/L | G | A/Q | N | H |
| WT 1-3 | L/V | Q/I | Q | V/N | Q | Q |
| WT 1-8 | I/I | Q/L | G | A/Q | N | Q |
| WT 1-22 | L/L | Y/I | N | V/Q | N | N |
| WT 1-35 | L/I | Q/L | G | A/N | Q | Q |
| WT 1-45 | L/V | Q/L | Q | V/Q | Q | Q |
| WT 1-48 | I/V | Y/I | Q | A/N | N | Q |
| WT 1-51 | I/V | Q/I | Q | A/Q | N | H |

TABLE 6

| affinity analysis data | | | |
|---|---|---|---|
| Site | KD (M) | Kon (1/Ms) | Kdis (1/S) |
| WT | 7.09E−08 | 4.80E+04 | 3.40E−03 |
| WT 1-3 | 5.17E−08 | 8.90E+03 | 4.60E−04 |
| WT 1-8 | 8.03E−08 | 6.09E+04 | 4.89E−03 |
| WT 1-22 | 9.96E−08 | 8.70E+03 | 8.67E−04 |
| WT 1-35 | 2.17E−08 | 4.20E+04 | 9.11E−04 |
| WT 1-45 | 6.76E−08 | 4.83E+04 | 3.27E−03 |
| WT 1-48 | 4.26E−08 | 1.36E+04 | 5.79E−04 |
| WT 1-51 | 3.54E−08 | 1.49E+04 | 5.27E−04 |

It is analyzed from Table 5 and Table 6 that, under a precondition of guaranteeing the antibody activity, the WT mutant sequences also have certain affinity.

Finally, it is to be noted that: the above embodiments each are only used to illustrate the technical schemes of the disclosure, but not intended to limit them; although the disclosure is described in detail with reference to the previous embodiments, it should be understood by those of ordinary skill in the art that: the technical schemes recorded in each of the previous embodiments may still be modified in the disclosure, or some or all of the technical features may be equivalently replaced; and these modifications or replacements do not make the essence of the corresponding technical schemes deviate from a scope of the technical schemes of each embodiment of the disclosure.

INDUSTRIAL APPLICABILITY

An isolated binding protein including an antigen binding domain bound with a cardiac troponin I provided by the disclosure includes specific heavy-chain CDR and light-chain CDR. The binding protein is capable of specifically recognizing and binding the cardiac troponin I protein, and has higher sensitivity and specificity. Particularly, the binding protein has high affinity with a human cTnI protein, thereby the detection and diagnosis of diseases related to the cardiac troponin I are achieved.

What is claimed is:

1. An isolated binding protein comprising an antigen binding domain, wherein the antigen binding domain comprises six complementarity determining regions of the following amino acid sequences, and has $K_D \leq 9.96 \times 10^{-8}$ mol/L affinity against a cTnI;

a complementarity determining region CDR-VH1 is SEQ ID NO:13: G-Y-X1-F-T-X2-Y-V-X3-H, wherein, the X1 is T, X2 is I or L, and the X3 is V, L or I;

a complementarity determining region CDR-VH2 is SEQ ID NO:14:Y-I-X1-P-Y-X2-D-G-T-X3-Y-N-E-K, wherein, the X1 is Q, N or Y, the X2 is I or L, and the X3 is K;

a complementarity determining region CDR-VH3 is SEQ ID NO:15:R-X1-G-Y-G-X2-Y-G-L-A, wherein the X1 is S, and the X2 is Q, N or G;

a complementarity determining region CDR-VL1 is SEQ ID NO:16:S-X1-G-A-X2-T-T-S-X3-Y-A-N, wherein, the X1 is T, the X2 is A or V, and the X3 is Q or N;

a complementarity determining region CDR-VL2 is SEQ ID NO:17:G-S-X1-N-R-X2-P, wherein, the X1 is N or Q, and the X2 is A;

a complementarity determining region CDR-VL3 is SEQ ID NO:18:A-X1-V-Y-S-N-X2-W, wherein, the X1 is L, and the X2 is Q, H or N.

2. The binding protein as claimed in claim 1, wherein the binding protein further comprises an antibody constant region sequence;

further, the constant region is derived from the mouse;

a light-chain constant region sequence is as shown in SEQ ID NO: 9; and a heavy-chain constant region sequence is as shown in SEQ ID NO: 10.

3. The binding protein as claimed in claim 1, wherein a mutation site of each complementarity determining region is selected from any one of the following mutation combinations:

| Site | CDR-VH1 X2/X3 | CDR-VH2 X1/X2 | CDR-VH3 X2 | CDR-VL1 X2/X3 | CDR-VL2 X1 | CDR-VL3 X2 |
|---|---|---|---|---|---|---|
| Mutation combination 1 | L/V | Q/L | G | A/Q | N | H |
| Mutation combination 2 | I/L | Q/I | N | A/N | Q | Q |
| Mutation combination 3 | I/I | Q/I | G | V/Q | N | N |
| Mutation combination 4 | L/V | Q/I | Q | V/N | Q | Q |
| Mutation combination 5 | L/L | Q/I | N | A/Q | N | N |
| Mutation combination 6 | L/I | Q/I | G | A/N | Q | H |
| Mutation combination 7 | I/V | Q/L | Q | V/Q | N | N |
| Mutation combination 8 | I/L | Q/L | N | V/N | Q | H |
| Mutation combination 9 | I/I | Q/L | G | A/Q | N | Q |
| Mutation combination 10 | L/V | Q/L | Q | A/N | Q | H |
| Mutation combination 11 | L/L | Q/L | N | V/Q | N | Q |
| Mutation combination 12 | L/I | N/I | G | V/N | Q | N |
| Mutation combination 13 | I/V | N/I | Q | A/Q | N | Q |
| Mutation combination 14 | I/L | N/I | N | A/N | Q | N |
| Mutation combination 15 | I/I | N/I | G | V/Q | N | H |
| Mutation combination 16 | L/V | N/I | Q | V/N | Q | N |
| Mutation combination 17 | L/L | N/L | N | A/Q | N | H |
| Mutation combination 18 | L/I | N/L | G | A/N | Q | Q |
| Mutation combination 19 | I/V | N/L | Q | V/Q | N | H |
| Mutation combination 20 | IL | N/L | N | V/N | Q | Q |
| Mutation combination 21 | I/I | Y/I | G | A/Q | N | N |
| Mutation combination 22 | L/V | Y/I | Q | A/N | Q | Q |
| Mutation combination 23 | L/L | Y/I | N | V/Q | N | N |
| Mutation combination 24 | L/I | Y/I | G | V/N | Q | H |
| Mutation combination 25 | I/V | Y/L | Q | A/Q | N | N |
| Mutation combination 26 | I/L | Y/L | N | A/N | Q | H |
| Mutation combination 27 | I/I | Y/L | G | V/Q | N | Q |
| Mutation combination 28 | L/V | Y/L | Q | V/N | Q | H |
| Mutation combination 29 | L/L | Y/L | N | A/Q | N | Q |
| Mutation combination 30 | L/I | Q/I | G | A/Q | Q | N |
| Mutation combination 31 | I/V | Q/L | Q | A/Q | N | Q |
| Mutation combination 32 | I/L | N/I | N | A/Q | Q | N |
| Mutation combination 33 | I/I | N/L | G | A/N | N | H |
| Mutation combination 34 | L/V | Y/I | G | A/Q | Q | N |
| Mutation combination 35 | L/L | Q/I | N | A/N | N | H |
| Mutation combination 36 | L/I | Q/L | G | A/N | Q | Q |
| Mutation combination 37 | I/V | N/I | Q | V/Q | N | H |
| Mutation combination 38 | I/L | N/L | N | V/Q | Q | Q |
| Mutation combination 39 | I/I | Y/I | G | V/Q | N | N |
| Mutation combination 40 | L/V | Q/L | Q | V/N | Q | Q |
| Mutation combination 41 | I/L | Q/L | N | V/N | N | N |
| Mutation combination 42 | L/I | N/I | N | V/N | Q | Q |
| Mutation combination 43 | L/V | N/L | Q | V/N | N | H |

-continued

| Site | CDR-VH1 X2/X3 | CDR-VH2 X1/X2 | CDR-VH3 X2 | CDR-VL1 X2/X3 | CDR-VL2 X1 | CDR-VL3 X2 |
|---|---|---|---|---|---|---|
| Mutation combination 44 | I/L | Y/I | N | A/Q | Q | Q |
| Mutation combination 45 | I/I | Q/I | G | A/N | N | N |
| Mutation combination 46 | L/V | Q/L | Q | V/Q | Q | Q |
| Mutation combination 47 | I/L | N/I | N | V/N | N | N |
| Mutation combination 48 | L/I | N/L | G | A/Q | Q | H |
| Mutation combination 49 | I/V | Y/I | Q | A/N | N | Q |
| Mutation combination 50 | L/L | N/L | N | V/Q | Q | N |
| Mutation combination 51 | I/I | Y/I | G | V/N | Q | H |
| Mutation combination 52 | I/V | Q/I | Q | A/Q | N | H |
| Mutation combination 53 | I/V | N/L | N | A/Q | N | N |
| Mutation combination 54 | I/V | Y/I | G | V/N | Q | Q |
| Mutation combination 55 | I/V | N/L | Q | A/N | N | Q |
| Mutation combination 56. | I/V | Y/I | G | V/Q | Q | N |

4. The binding protein as claimed in claim 1, wherein the binding protein is one of F(ab')2, Fab', Fab, Fv, scFv, and a bispecific antibody.

5. The binding protein as claimed in claim 1, wherein the binding protein comprises light-chain framework regions FR-L1, FR-L2, FR-L3 and FR-L4 of which sequences are successively shown in SEQ ID NO: 1-4, and/or heavy-chain framework regions FR-H1, FR-H2, FR-H3 and FR-H4 of which sequences are successively shown in SEQ ID NO: 5-8.

6. The binding protein as claimed in claim 1, wherein the constant region sequence is selected from a sequence of any one constant region of IgG1, IgG2, IgG3, IgG4, IgA, IgM, IgE, and IgD.

7. The binding protein as claimed in claim 1, wherein a species source of the constant region is cattle, horse, dairy cow, pig, sheep, goat, rat, mouse, dog, cat, rabbit, camel, donkey, deer, mink, chicken, duck, goose, turkey, gamecock or human.

8. The binding protein as claimed in claim 1, wherein the binding protein is labeled by an indicator which shows signal intensity.

9. A kit, wherein the kit comprises one or more of the binding proteins as claimed in claim 1.

10. An isolated nucleic acid, wherein the binding protein as claimed in claim 1 is encoded by the nucleic acid.

11. A vector, wherein the vector comprises the nucleic acid as claimed in claim 10.

12. A host cell, wherein the host cell comprises the nucleic acid as claimed in claim 10.

13. A method for producing the binding protein as claimed in claim 1, wherein the method comprises the following steps:

culturing a host cell comprising a nucleic acid encoding the binding protein as claimed in claim 1 in a culture medium, and recovering the generated binding protein from the culture medium or from the cultured host cells.

14. A method for detecting a troponin I antigen in a test sample, comprising:

a) in a condition sufficient for an antibody/antigen binding reaction, enabling the troponin I antigen in the test sample to contact with the binding protein as claimed in claim 1 to form an immune complex; and b) detecting the presence of the immune complex, the presence of the immune complex indicates the presence of the troponin I antigen in the test sample;

the troponin I antigen is a cardiac troponin I antigen.

15. The method as claimed in claim 14, wherein the method is based on a fluorescence immunoassay, a chemiluminescence technology, a colloidal gold immunotechnology, a radioimmunoassay and/or an enzyme-linked immunoassay.

16. The method as claimed in claim 14, wherein the test sample is selected from at least one of whole blood, peripheral blood, serum, plasma or a myocardial tissue.

17. The method as claimed in claim 14, wherein the subject which the test sample is derived from is a mammal.

18. The method as claimed in claim 14, wherein the presence of the immune complex indicates the presence of the disease related to the cardiac troponin I.

19. The method as claimed in claim 14, wherein in the step a), the immune complex further comprises a second antibody, and the second antibody is bound with the troponin I antigen.

* * * * *

SEQUENCE LISTING

```
<160> NUMBER OF SEQ ID NOS: 28

<210> SEQ ID NO 1
<211> LENGTH: 24
<212> TYPE: PRT
<213> ORGANISM: Mus musculus

<400> SEQUENCE: 1

Gln Ala Val Val Ile Gln Glu Ser Ala Leu Thr Thr Ser Pro Gly Glu
1               5                   10                  15

Thr Val Thr Leu Thr Cys Arg Ser
            20


<210> SEQ ID NO 2
<211> LENGTH: 15
<212> TYPE: PRT
<213> ORGANISM: Mus musculus

<400> SEQUENCE: 2

Trp Val Gln Glu Lys Pro Asp His Leu Phe Thr Gly Leu Ile Gly
1               5                   10                  15


<210> SEQ ID NO 3
<211> LENGTH: 32
<212> TYPE: PRT
<213> ORGANISM: Mus musculus

<400> SEQUENCE: 3

Gly Val Pro Ala Arg Phe Ser Gly Ser Leu Ile Gly Asp Lys Ala Ala
1               5                   10                  15

Leu Thr Ile Thr Gly Ala Gln Thr Glu Asp Glu Ala Ile Tyr Phe Cys
            20                  25                  30


<210> SEQ ID NO 4
<211> LENGTH: 17
<212> TYPE: PRT
<213> ORGANISM: Mus musculus

<400> SEQUENCE: 4

Val Phe Gly Gly Gly Thr Lys Leu Thr Val Leu Gly Gln Pro Lys Ser
1               5                   10                  15

Ser


<210> SEQ ID NO 5
<211> LENGTH: 25
<212> TYPE: PRT
<213> ORGANISM: Mus musculus

<400> SEQUENCE: 5

Glu Val Gln Leu Gln Gln Ser Gly Pro Glu Leu Val Lys Pro Gly Ala
1               5                   10                  15

Ser Val Lys Met Ser Cys Lys Ala Ser
            20                  25
```

<210> SEQ ID NO 6
<211> LENGTH: 14
<212> TYPE: PRT
<213> ORGANISM: Mus musculus

<400> SEQUENCE: 6

Trp Val Lys Gln Lys Pro Gly Gln Gly Leu Glu Trp Ile Gly
1 5 10

<210> SEQ ID NO 7
<211> LENGTH: 34
<212> TYPE: PRT
<213> ORGANISM: Mus musculus

<400> SEQUENCE: 7

Phe Lys Gly Lys Ala Thr Leu Thr Val Asp Lys Ser Ser Ser Thr Ala
1 5 10 15

Phe Met Glu Leu Ser Ser Leu Thr Ser Glu Asp Ser Ala Val Tyr Tyr
20 25 30

Cys Ala

<210> SEQ ID NO 8
<211> LENGTH: 15
<212> TYPE: PRT
<213> ORGANISM: Mus musculus

<400> SEQUENCE: 8

Trp Leu Ala Tyr Trp Gly Gln Gly Thr Leu Val Thr Val Ser Ala
1 5 10 15

<210> SEQ ID NO 9
<211> LENGTH: 101
<212> TYPE: PRT
<213> ORGANISM: Mus musculus

<400> SEQUENCE: 9

Pro Ser Val Thr Leu Phe Pro Pro Ser Ser Glu Glu Leu Glu Thr Asn
1 5 10 15

Lys Ala Thr Leu Val Cys Thr Ile Thr Asp Phe Tyr Pro Gly Val Val
20 25 30

Thr Val Asp Trp Lys Val Asp Gly Thr Pro Val Thr Gln Gly Met Glu
35 40 45

Thr Thr Gln Pro Ser Lys Gln Ser Asn Asn Lys Tyr Met Ala Ser Ser
50 55 60

Tyr Leu Thr Leu Thr Ala Arg Ala Trp Glu Arg His Ser Ser Tyr Ser
65 70 75 80

Cys Gln Val Thr His Glu Gly His Thr Val Glu Lys Ser Leu Ser Arg
85 90 95

Ala Asp Cys Ser Phe
100

<210> SEQ ID NO 10
<211> LENGTH: 335
<212> TYPE: PRT
<213> ORGANISM: Mus musculus

<400> SEQUENCE: 10

Ala Lys Thr Thr Pro Pro Ser Val Tyr Pro Leu Ala Pro Gly Cys Gly
1 5 10 15

Asp Thr Thr Gly Ser Ser Val Thr Leu Gly Cys Leu Val Lys Gly Tyr

```
            20                  25                  30

Phe Pro Glu Ser Val Thr Val Thr Trp Asn Ser Gly Ser Leu Ser Ser
        35                  40                  45

Ser Val His Thr Phe Pro Ala Leu Leu Gln Ser Gly Leu Tyr Thr Met
    50                  55                  60

Ser Ser Ser Val Thr Val Pro Ser Ser Thr Trp Pro Ser Gln Thr Val
65                  70                  75                  80

Thr Cys Ser Val Ala His Pro Ala Ser Ser Thr Thr Val Asp Lys Lys
                85                  90                  95

Leu Glu Pro Ser Gly Pro Ile Ser Thr Ile Asn Pro Cys Pro Pro Cys
            100                 105                 110

Lys Glu Cys His Lys Cys Pro Ala Pro Asn Leu Glu Gly Gly Pro Ser
        115                 120                 125

Val Phe Ile Phe Pro Pro Asn Ile Lys Asp Val Leu Met Ile Ser Leu
    130                 135                 140

Thr Pro Lys Val Thr Cys Val Val Val Asp Val Ser Glu Asp Asp Pro
145                 150                 155                 160

Asp Val Gln Ile Ser Trp Phe Val Asn Asn Val Glu Val His Thr Ala
                165                 170                 175

Gln Thr Gln Thr His Arg Glu Asp Tyr Asn Ser Thr Ile Arg Val Val
            180                 185                 190

Ser Thr Leu Pro Ile Gln His Gln Asp Trp Met Ser Gly Lys Glu Phe
        195                 200                 205

Lys Cys Lys Val Asn Asn Lys Asp Leu Pro Ser Pro Ile Glu Arg Thr
    210                 215                 220

Ile Ser Lys Ile Lys Gly Leu Val Arg Ala Pro Gln Val Tyr Ile Leu
225                 230                 235                 240

Pro Pro Pro Ala Glu Gln Leu Ser Arg Lys Asp Val Ser Leu Thr Cys
                245                 250                 255

Leu Val Val Gly Phe Asn Pro Gly Asp Ile Ser Val Glu Trp Thr Ser
            260                 265                 270

Asn Gly His Thr Glu Glu Asn Tyr Lys Asp Thr Ala Pro Val Leu Asp
        275                 280                 285

Ser Asp Gly Ser Tyr Phe Ile Tyr Ser Lys Leu Asn Met Lys Thr Ser
    290                 295                 300

Lys Trp Glu Lys Thr Asp Ser Phe Ser Cys Asn Val Arg His Glu Gly
305                 310                 315                 320

Leu Lys Asn Tyr Tyr Leu Lys Lys Thr Ile Ser Arg Ser Pro Gly
                325                 330                 335


<210> SEQ ID NO 11
<211> LENGTH: 216
<212> TYPE: PRT
<213> ORGANISM: Mus musculus

<400> SEQUENCE: 11

Gln Ala Val Val Ile Gln Glu Ser Ala Leu Thr Thr Ser Pro Gly Glu
1               5                   10                  15

Thr Val Thr Leu Thr Cys Arg Ser Ser Ser Gly Ala Ala Thr Thr Ser
            20                  25                  30

Gln Tyr Ala Asn Trp Val Gln Glu Lys Pro Asp His Leu Phe Thr Gly
        35                  40                  45

Leu Ile Gly Gly Ser Asn Asn Arg Ala Pro Gly Val Pro Ala Arg Phe
    50                  55                  60
```

```
Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Ile Val Tyr Ser Asn
                85                  90                  95

His Trp Val Phe Gly Gly Gly Thr Lys Leu Thr Val Leu Gly Gln Pro
            100                 105                 110

Lys Ser Ser Pro Ser Val Thr Leu Phe Pro Pro Ser Ser Glu Glu Leu
        115                 120                 125

Glu Thr Asn Lys Ala Thr Leu Val Cys Thr Ile Thr Asp Phe Tyr Pro
    130                 135                 140

Gly Val Val Thr Val Asp Trp Lys Val Asp Gly Thr Pro Val Thr Gln
145                 150                 155                 160

Gly Met Glu Thr Thr Gln Pro Ser Lys Gln Ser Asn Asn Lys Tyr Met
                165                 170                 175

Ala Ser Ser Tyr Leu Thr Leu Thr Ala Arg Ala Trp Glu Arg His Ser
            180                 185                 190

Ser Tyr Ser Cys Gln Val Thr His Glu Gly His Thr Val Glu Lys Ser
        195                 200                 205

Leu Ser Arg Ala Asp Cys Ser Phe
    210                 215


<210> SEQ ID NO 12
<211> LENGTH: 457
<212> TYPE: PRT
<213> ORGANISM: Mus musculus

<400> SEQUENCE: 12

Glu Val Gln Leu Gln Gln Ser Gly Pro Glu Leu Val Lys Pro Gly Ala
1               5                   10                  15

Ser Val Lys Met Ser Cys Lys Ala Ser Gly Tyr Ser Phe Thr Leu Tyr
            20                  25                  30

Val Val His Trp Val Lys Gln Lys Pro Gly Gln Gly Leu Glu Trp Ile
        35                  40                  45

Gly Tyr Ile Gln Pro Tyr Leu Asp Gly Thr Arg Tyr Asn Glu Lys Phe
    50                  55                  60

Lys Gly Lys Ala Thr Leu Thr Val Asp Lys Ser Ser Ser Thr Ala Phe
65                  70                  75                  80

Met Glu Leu Ser Ser Leu Thr Ser Glu Asp Ser Ala Val Tyr Tyr Cys
                85                  90                  95

Ala Arg Thr Gly Tyr Gly Gly Tyr Gly Leu Ala Trp Leu Ala Tyr Trp
            100                 105                 110

Gly Gln Gly Thr Leu Val Thr Val Ser Ala Ala Lys Thr Thr Pro Pro
        115                 120                 125

Ser Val Tyr Pro Leu Ala Pro Gly Cys Gly Asp Thr Thr Gly Ser Ser
    130                 135                 140

Val Thr Leu Gly Cys Leu Val Lys Gly Tyr Phe Pro Glu Ser Val Thr
145                 150                 155                 160

Val Thr Trp Asn Ser Gly Ser Leu Ser Ser Ser Val His Thr Phe Pro
                165                 170                 175

Ala Leu Leu Gln Ser Gly Leu Tyr Thr Met Ser Ser Ser Val Thr Val
            180                 185                 190

Pro Ser Ser Thr Trp Pro Ser Gln Thr Val Thr Cys Ser Val Ala His
        195                 200                 205

Pro Ala Ser Ser Thr Thr Val Asp Lys Lys Leu Glu Pro Ser Gly Pro
    210                 215                 220
```

```
Ile Ser Thr Ile Asn Pro Cys Pro Pro Cys Lys Glu Cys His Lys Cys
225                 230                 235                 240

Pro Ala Pro Asn Leu Glu Gly Gly Pro Ser Val Phe Ile Phe Pro Pro
                245                 250                 255

Asn Ile Lys Asp Val Leu Met Ile Ser Leu Thr Pro Lys Val Thr Cys
            260                 265                 270

Val Val Val Asp Val Ser Glu Asp Asp Pro Asp Val Gln Ile Ser Trp
        275                 280                 285

Phe Val Asn Asn Val Glu Val His Thr Ala Gln Thr Gln Thr His Arg
    290                 295                 300

Glu Asp Tyr Asn Ser Thr Ile Arg Val Val Ser Thr Leu Pro Ile Gln
305                 310                 315                 320

His Gln Asp Trp Met Ser Gly Lys Glu Phe Lys Cys Lys Val Asn Asn
                325                 330                 335

Lys Asp Leu Pro Ser Pro Ile Glu Arg Thr Ile Ser Lys Ile Lys Gly
            340                 345                 350

Leu Val Arg Ala Pro Gln Val Tyr Ile Leu Pro Pro Pro Ala Glu Gln
        355                 360                 365

Leu Ser Arg Lys Asp Val Ser Leu Thr Cys Leu Val Val Gly Phe Asn
    370                 375                 380

Pro Gly Asp Ile Ser Val Glu Trp Thr Ser Asn Gly His Thr Glu Glu
385                 390                 395                 400

Asn Tyr Lys Asp Thr Ala Pro Val Leu Asp Ser Asp Gly Ser Tyr Phe
                405                 410                 415

Ile Tyr Ser Lys Leu Asn Met Lys Thr Ser Lys Trp Glu Lys Thr Asp
            420                 425                 430

Ser Phe Ser Cys Asn Val Arg His Glu Gly Leu Lys Asn Tyr Tyr Leu
        435                 440                 445

Lys Lys Thr Ile Ser Arg Ser Pro Gly
    450                 455
```

```
<210> SEQ ID NO 13
<211> LENGTH: 10
<212> TYPE: PRT
<213> ORGANISM: Artificial Sequence
<220> FEATURE:
<223> OTHER INFORMATION: mutated CDR-VH1
<220> FEATURE:
<221> NAME/KEY: MISC_FEATURE
<222> LOCATION: (3)..(3)
<223> OTHER INFORMATION: Xaa is S or T
<220> FEATURE:
<221> NAME/KEY: MISC_FEATURE
<222> LOCATION: (6)..(6)
<223> OTHER INFORMATION: Xaa is I or L
<220> FEATURE:
<221> NAME/KEY: MISC_FEATURE
<222> LOCATION: (9)..(9)
<223> OTHER INFORMATION: Xaa is V, L or I

<400> SEQUENCE: 13

Gly Tyr Xaa Phe Thr Xaa Tyr Val Xaa His
1               5                   10


<210> SEQ ID NO 14
<211> LENGTH: 14
<212> TYPE: PRT
<213> ORGANISM: Artificial Sequence
<220> FEATURE:
<223> OTHER INFORMATION: mutated CDR-VH2
<220> FEATURE:
```

<221> NAME/KEY: MISC_FEATURE
<222> LOCATION: (3)..(3)
<223> OTHER INFORMATION: Xaa is Q, N or Y
<220> FEATURE:
<221> NAME/KEY: MISC_FEATURE
<222> LOCATION: (6)..(6)
<223> OTHER INFORMATION: Xaa is I or L
<220> FEATURE:
<221> NAME/KEY: MISC_FEATURE
<222> LOCATION: (10)..(10)
<223> OTHER INFORMATION: Xaa is R or K

<400> SEQUENCE: 14

Tyr Ile Xaa Pro Tyr Xaa Asp Gly Thr Xaa Tyr Asn Glu Lys
1 5 10

<210> SEQ ID NO 15
<211> LENGTH: 10
<212> TYPE: PRT
<213> ORGANISM: Artificial Sequence
<220> FEATURE:
<223> OTHER INFORMATION: mutated CDR-VH3
<220> FEATURE:
<221> NAME/KEY: MISC_FEATURE
<222> LOCATION: (2)..(2)
<223> OTHER INFORMATION: Xaa is S or T
<220> FEATURE:
<221> NAME/KEY: MISC_FEATURE
<222> LOCATION: (6)..(6)
<223> OTHER INFORMATION: Xaa is Q, N or G

<400> SEQUENCE: 15

Arg Xaa Gly Tyr Gly Xaa Tyr Gly Leu Ala
1 5 10

<210> SEQ ID NO 16
<211> LENGTH: 12
<212> TYPE: PRT
<213> ORGANISM: Artificial Sequence
<220> FEATURE:
<223> OTHER INFORMATION: mutated CDR-VL1
<220> FEATURE:
<221> NAME/KEY: MISC_FEATURE
<222> LOCATION: (2)..(2)
<223> OTHER INFORMATION: Xaa is S or T
<220> FEATURE:
<221> NAME/KEY: MISC_FEATURE
<222> LOCATION: (5)..(5)
<223> OTHER INFORMATION: Xaa is A or V
<220> FEATURE:
<221> NAME/KEY: MISC_FEATURE
<222> LOCATION: (9)..(9)
<223> OTHER INFORMATION: Xaa is Q or N

<400> SEQUENCE: 16

Ser Xaa Gly Ala Xaa Thr Thr Ser Xaa Tyr Ala Asn
1 5 10

<210> SEQ ID NO 17
<211> LENGTH: 7
<212> TYPE: PRT
<213> ORGANISM: Artificial Sequence
<220> FEATURE:
<223> OTHER INFORMATION: mutated CDR-VL2
<220> FEATURE:
<221> NAME/KEY: MISC_FEATURE
<222> LOCATION: (3)..(3)
<223> OTHER INFORMATION: Xaa is N or Q
<220> FEATURE:
<221> NAME/KEY: MISC_FEATURE
<222> LOCATION: (6)..(6)
<223> OTHER INFORMATION: Xaa is A or V

<400> SEQUENCE: 17

Gly Ser Xaa Asn Arg Xaa Pro
1 5

<210> SEQ ID NO 18
<211> LENGTH: 8
<212> TYPE: PRT
<213> ORGANISM: Artificial Sequence
<220> FEATURE:
<223> OTHER INFORMATION: mutated CDR-VL3
<220> FEATURE:
<221> NAME/KEY: MISC_FEATURE
<222> LOCATION: (2)..(2)
<223> OTHER INFORMATION: Xaa is I or L
<220> FEATURE:
<221> NAME/KEY: MISC_FEATURE
<222> LOCATION: (7)..(7)
<223> OTHER INFORMATION: Xaa is Q, H or N

<400> SEQUENCE: 18

Ala Xaa Val Tyr Ser Asn Xaa Trp
1 5

<210> SEQ ID NO 19
<211> LENGTH: 25
<212> TYPE: DNA
<213> ORGANISM: Artificial Sequence
<220> FEATURE:
<223> OTHER INFORMATION: SMARTER II A oligonucleotide from a commerical kit
<220> FEATURE:
<221> NAME/KEY: misc_feature
<222> LOCATION: (25)..(25)
<223> OTHER INFORMATION: XXXXX at the 3'-end

<400> SEQUENCE: 19
aagcagtggt atcaacgcag agtac 25

<210> SEQ ID NO 20
<211> LENGTH: 27
<212> TYPE: DNA
<213> ORGANISM: Artificial Sequence
<220> FEATURE:
<223> OTHER INFORMATION: 5'-RACE CDS primer
<220> FEATURE:
<221> NAME/KEY: misc_feature
<222> LOCATION: (26)..(26)
<223> OTHER INFORMATION: V=A, G, or C
<220> FEATURE:
<221> NAME/KEY: misc_feature
<222> LOCATION: (27)..(27)
<223> OTHER INFORMATION: N=A, C, G, or T

<400> SEQUENCE: 20
tttttttttt tttttttttt tttttvn 27

<210> SEQ ID NO 21
<211> LENGTH: 45
<212> TYPE: DNA
<213> ORGANISM: Artificial Sequence
<220> FEATURE:
<223> OTHER INFORMATION: universal primer A mixture

<400> SEQUENCE: 21
ctaatacgac tcactatagg gcaagcagtg gtatcaacgc agagt 45

<210> SEQ ID NO 22
<211> LENGTH: 23
<212> TYPE: DNA

<213> ORGANISM: Artificial Sequence
<220> FEATURE:
<223> OTHER INFORMATION: nested universal primer A

<400> SEQUENCE: 22
aagcagtggt atcaacgcag agt 23

<210> SEQ ID NO 23
<211> LENGTH: 26
<212> TYPE: DNA
<213> ORGANISM: Artificial Sequence
<220> FEATURE:
<223> OTHER INFORMATION: MIgG-CKR

<400> SEQUENCE: 23
cgcctaacac tcattcctgt tgaagc 26

<210> SEQ ID NO 24
<211> LENGTH: 22
<212> TYPE: DNA
<213> ORGANISM: Artificial Sequence
<220> FEATURE:
<223> OTHER INFORMATION: MIgG-CHR

<400> SEQUENCE: 24
ccgctcattt acccggagac cg 22

<210> SEQ ID NO 25
<211> LENGTH: 46
<212> TYPE: DNA
<213> ORGANISM: Artificial Sequence
<220> FEATURE:
<223> OTHER INFORMATION: cTnI-21C5-HF

<400> SEQUENCE: 25
cccaagcttg ccgccaccat gagtgtgctc actcaggtcc tggggt 46

<210> SEQ ID NO 26
<211> LENGTH: 40
<212> TYPE: DNA
<213> ORGANISM: Artificial Sequence
<220> FEATURE:
<223> OTHER INFORMATION: cTnI-21C5-HR

<400> SEQUENCE: 26
ggggaattct catttacccg gagaccggga gatggtcttc 40

<210> SEQ ID NO 27
<211> LENGTH: 45
<212> TYPE: DNA
<213> ORGANISM: Artificial Sequence
<220> FEATURE:
<223> OTHER INFORMATION: cTnI-21C5-LF

<400> SEQUENCE: 27
cccaagcttg ccgccaccat gaagtcacag acccaggtct tcgta 45

<210> SEQ ID NO 28
<211> LENGTH: 43
<212> TYPE: DNA
<213> ORGANISM: Artificial Sequence
<220> FEATURE:
<223> OTHER INFORMATION: cTnI-21C5-LR -continued

```
<400> SEQUENCE: 28

cccgaattct caacactcat tcctgttgaa gctcttgacg atg                    43
```